(12) United States Patent
Walsh et al.

(10) Patent No.: US 7,511,265 B2
(45) Date of Patent: Mar. 31, 2009

(54) METHOD AND APPARATUS FOR ACCURATE CALIBRATION OF A REFLECTOMETER BY USING A RELATIVE REFLECTANCE MEASUREMENT

(75) Inventors: Phillip Walsh, Austin, TX (US); Dale A. Harrison, Austin, TX (US)

(73) Assignee: MetroSol, Inc., Austin, TX (US)

( * ) Notice: Subject to any disclaimer, the term of this patent is extended or adjusted under 35 U.S.C. 154(b) by 341 days.

(21) Appl. No.: 11/418,846

(22) Filed: May 5, 2006

(65) Prior Publication Data
US 2007/0181795 A1    Aug. 9, 2007

Related U.S. Application Data

(63) Continuation-in-part of application No. 10/930,339, filed on Aug. 31, 2004.

(60) Provisional application No. 60/600,599, filed on Aug. 11, 2004.

(51) Int. Cl.
*G01N 21/55* (2006.01)
(52) U.S. Cl. .................... 250/252.1; 356/448
(58) Field of Classification Search .............. 250/252.1; 356/448
See application file for complete search history.

(56) References Cited

U.S. PATENT DOCUMENTS

| | | |
|---|---|---|
| 3,091,154 A | 5/1963 | Hall |
| 3,160,752 A | 12/1964 | Bennett |
| 3,572,951 A | 3/1971 | Rothwarf et al. |
| 3,751,643 A * | 8/1973 | Dill et al. ............... 702/172 |
| 3,825,347 A | 7/1974 | Kaiser |

(Continued)

FOREIGN PATENT DOCUMENTS

| WO | WO 2007126612 A2 * | 11/2007 |
|---|---|---|
| WO | WO 2007130295 A2 * | 11/2007 |

OTHER PUBLICATIONS

McPherson Product Brochure "Reflectometer for Sample Analysis," McPherson, Inc., Massachusetts, Published Prior to Sep. 23, 2003, 1-2 pps.

(Continued)

*Primary Examiner*—David P Porta
*Assistant Examiner*—David S Baker
(74) *Attorney, Agent, or Firm*—O'Keefe, Egan, Peterman & Enders LLP

(57) ABSTRACT

A reflectometer calibration technique is provided that may include the use of two calibration samples in the calibration process. Further, the technique allows for calibration even in the presence of variations between the actual and assumed properties of at least one or more of the calibration samples. In addition, the technique utilizes a ratio of the measurements from the first and second calibration samples to determine the actual properties of at least one of the calibration samples. The ratio may be a ratio of the intensity reflected from the first and second calibration samples. The samples may exhibit relatively different reflective properties at the desired wavelengths. In such a technique the reflectance data of each sample may then be considered relatively decoupled from the other and actual properties of one or more of the calibration samples may be calculated. The determined actual properties may then be utilized to assist calibration of the reflectometer.

41 Claims, 20 Drawing Sheets

U.S. PATENT DOCUMENTS

| | | | |
|---|---|---|---|
| 4,029,419 A | 6/1977 | Schumann et al. | |
| 4,368,983 A | 1/1983 | Bennett | |
| 4,645,349 A | 2/1987 | Tabata | |
| 4,729,657 A | 3/1988 | Cooper et al. | |
| 4,899,055 A | 2/1990 | Adams | |
| 4,984,894 A | 1/1991 | Kondo | |
| 5,042,949 A | 8/1991 | Greenberg et al. | |
| 5,045,704 A | 9/1991 | Coates | |
| 5,182,618 A | 1/1993 | Heinonen | |
| 5,241,366 A * | 8/1993 | Bevis et al. | 356/632 |
| 5,251,006 A | 10/1993 | Hongis et al. | |
| 5,357,448 A | 10/1994 | Stanford | |
| RE34,783 E | 11/1994 | Coates | |
| 5,440,141 A | 8/1995 | Horie | |
| 5,452,091 A | 9/1995 | Johnson | |
| 5,486,701 A | 1/1996 | Norton et al. | |
| 5,493,401 A | 2/1996 | Horie et al. | |
| 5,581,350 A | 12/1996 | Chen et al. | |
| 5,607,800 A | 3/1997 | Ziger | |
| 5,608,526 A | 3/1997 | Piwonka-Corle et al. | |
| 5,686,993 A | 11/1997 | Kokubo et al. | |
| 5,747,813 A | 5/1998 | Norton et al. | |
| 5,771,094 A | 6/1998 | Carter | |
| 5,781,304 A | 7/1998 | Kotidis et al. | |
| 5,798,837 A | 8/1998 | Aspnes et al. | |
| 5,880,831 A | 3/1999 | Buermann et al. | |
| 5,900,939 A | 5/1999 | Aspnes et al. | |
| 5,917,594 A | 6/1999 | Norton | |
| 5,991,022 A | 11/1999 | Buermann et al. | |
| 6,091,485 A | 7/2000 | Li et al. | |
| 6,128,085 A | 10/2000 | Buermann et al. | |
| 6,181,427 B1 | 1/2001 | Yarussi et al. | |
| 6,184,529 B1 | 2/2001 | Contini | |
| 6,184,984 B1 | 2/2001 | Lee | |
| 6,261,853 B1 | 7/2001 | Howell et al. | |
| 6,278,519 B1 | 8/2001 | Rosencwaig et al. | |
| 6,297,880 B1 | 10/2001 | Rosencwaig et al. | |
| 6,304,326 B1 | 10/2001 | Aspnes et al. | |
| 6,313,466 B1 | 11/2001 | Olsen et al. | |
| 6,392,756 B1 * | 5/2002 | Li et al. | 356/632 |
| 6,411,385 B2 | 6/2002 | Aspnes et al. | |
| 6,414,302 B1 | 7/2002 | Freeouf | |
| 6,417,921 B2 | 7/2002 | Rosencwaig et al. | |
| 6,453,006 B1 | 9/2002 | Koppel | |
| 6,485,872 B1 | 11/2002 | Rosenthal et al. | |
| 6,525,829 B1 | 2/2003 | Powell et al. | |
| 6,549,279 B2 | 4/2003 | Adams et al. | |
| 6,630,673 B2 | 10/2003 | Khalil et al. | |
| 6,643,354 B2 | 11/2003 | Koppel | |
| 6,657,737 B2 * | 12/2003 | Kimba et al. | 356/630 |
| 6,710,865 B2 | 3/2004 | Forouhi et al. | |
| 6,713,775 B2 * | 3/2004 | Chelvayohan et al. | 250/559.16 |
| 6,734,968 B1 | 5/2004 | Wang et al. | |
| 6,765,676 B1 | 7/2004 | Buermann | |
| 6,768,785 B2 | 7/2004 | Koppel | |
| 6,934,025 B2 | 8/2005 | Opsal et al. | |
| 6,987,832 B2 | 1/2006 | Koppel | |
| 7,072,050 B2 | 7/2006 | Kimba et al. | |
| 7,282,703 B2 * | 10/2007 | Walsh et al. | 250/252.1 |
| 7,399,975 B2 * | 7/2008 | Harrison | 250/372 |
| 2001/0055118 A1 | 12/2001 | Nawracala | |
| 2002/0030826 A1 | 3/2002 | Chalmers et al. | |
| 2002/0110218 A1 | 8/2002 | Koppel | |
| 2002/0149774 A1 | 10/2002 | McAninch | |
| 2002/0154302 A1 | 10/2002 | Rosencwaig | |
| 2002/0179864 A1 | 12/2002 | Fielden | |
| 2002/0179867 A1 | 12/2002 | Fielden | |
| 2002/0180961 A1 | 12/2002 | Wack | |
| 2002/0180985 A1 | 12/2002 | Wack | |
| 2002/0180986 A1 | 12/2002 | Nikoonahad | |
| 2002/0182760 A1 | 12/2002 | Wack | |
| 2002/0190207 A1 | 12/2002 | Levy | |
| 2003/0011786 A1 | 1/2003 | Levy | |
| 2003/0071996 A1 | 4/2003 | Wang et al. | |
| 2004/0032593 A1 | 2/2004 | Venugopal | |
| 2004/0052330 A1 | 3/2004 | Koppel | |
| 2004/0150820 A1 | 8/2004 | Nikoonahad et al. | |
| 2004/0218717 A1 | 11/2004 | Koppel | |
| 2005/0036143 A1 | 2/2005 | Huang | |
| 2006/0192958 A1 * | 8/2006 | Harrison | 356/328 |
| 2007/0181794 A1 * | 8/2007 | Walsh et al. | 250/252.1 |
| 2007/0182970 A1 * | 8/2007 | Harrison | 356/503 |
| 2007/0215801 A1 * | 9/2007 | Walsh et al. | 250/252.1 |
| 2008/0073560 A1 * | 3/2008 | Harrison et al. | 250/431 |

OTHER PUBLICATIONS

McPherson Product Brochure "Spectral Reflectometer," McPherson, Inc., Massachusetts, Nov. 12, 2001, 1 pg.

McPherson Product Brochure "VUVaS Spectrophotometers for 115 nm to >380 nm," McPherson, Inc., Massachusetts, Published Prior to Sep. 23, 2003, 1-4 pps.

McPherson Product Brochure "VUVaS Spectrophotometers, Made to Measure 115-380 nm," McPherson, Inc., Massachusetts, Published Prior to Sep. 23, 2003, 1-8 pps.

Acton Research Product Brochure "Acton Research Purged DAMS Optical Measurement System," Acton Research Corporation, Massachusetts, Published Prior to Sep. 23, 2003, 1-2 pps.

"The Thin Film tool for next generation lithography at 157nm," Web page from http://www.sopra-sa.com, Sopra, Printed From Internet On Feb. 19, 2002, 1pg.

"SE and GXR combined on the same instrument," Web page from http://www.sopra-sa.com, Sopra, Printed From Internet on Feb. 19, 2002, 1pg.

"The ideal Thin Film characterization unit for Development and Pilot Line environment," Web page from http://www.sopra-sa.com, Sopra, Printed From Internet on Feb. 19, 2002, 1 pg.

"VUV-VASE™, The Award Winning VUV-VASE™ is the latest addition to our line of Spectroscopic Ellipsometers," Web pages from http://www.jawoolam.com, J.A. Woollam Company, Nebraska, Printed From Internet on Nov. 5, 2002, 1-2 pps.

"Vacuum UV Spectroscopic Ellipsometers," Web pages from http://www.sentech.de, Sentech Instruments, Printed From Internet on Feb. 20, 2002, 1-3 pps.

Search Report;PCT/US04/30859; 13 pgs.

Rubloff, "Surface Reflectance Spectroscopy System", Technical Disclosure, Ip.com, www.ip.com, May 1, 1977, 5 pgs.

Copending Application, entitled "Method And Apparatus For Performing Highly Accurate Thin Film Measurement", U.S. Appl. No. 10/930,219, filed Aug. 31, 2004; 53 pgs.

Copending Application, entitled "Method And Apparatus For Accurate Calibration Of A Reflectometer By Using A Relative Reflectance Measurement", U.S. Appl. No. 11/418,827, filed May 5, 2006; 66 pgs.

Copending Application, entitled "Method And Apparatus For Accurate Calibration Of VUV Reflectrometer", U.S. Appl. No. 10/930,339, filed Aug. 31, 2004; 51 pgs.

Copending Application, entitled "Method And Apparatus For Accurate Calibration Of A Reflectometer By Using A Relative Reflectance Measurement", U.S. Appl. No. 11/789,686, filed Apr. 25, 2007; 93 pgs.

Field et al., "Method Of Using The Reflectance Ratios Of Different Angles Of Incidence For The Determination Of Optical Constants", Applied Optics, vol. 10, No. 6, Jun. 1971, 4 pgs.

Hunter et al., "Thickness Of Absorbing Films Necessary To Measure Their Optical Constants Using The Reflectance-Vs-Angle-Of-Incidence Method", Journal Of The Optical Society Of America, vol. 64, No. 4, Apr. 1874, 5 pgs.

Hunter et al., "Journal Of The Optical Society Of America", Optical Society Of America, vol. 55, No. 10, Part 1, Oct. 1965, 8 pgs.

Search Report, PCT/US2007/010003, Dec. 17, 2008, 3 pgs.

* cited by examiner

METHOD AND APPARATUS FOR ACCURATE CALIBRATION OF A REFLECTOMETER BY USING A RELATIVE REFLECTANCE MEASUREMENT

CROSS-REFERENCE TO RELATED APPLICATIONS

This application is a continuation-in-part application of U.S. patent application Ser. No. 10/930,339 filed Aug. 31, 2004 which claims priority to Provisional Patent Application No. 60/600,599 filed Aug. 11, 2004; the disclosures of which are each expressly incorporated herein by reference.

BACKGROUND OF THE INVENTION

The present invention relates to the field of optical metrology. More specifically, it provides a method by which reflectance data may be accurately calibrated. In one embodiment it provides a method by which broad-band vacuum ultraviolet (VUV) reflectance data may be accurately calibrated. Additionally, it also provides a method by which highly accurate thin film measurements may be performed.

Optical reflectometry techniques have long been employed in process control applications in the semiconductor manufacturing industry due to their non-contact, non-destructive and generally high-throughput nature. The vast majority of these tools operate in some portion of the spectral region spanning the deep ultraviolet and near-infrared wavelengths (DUV-NIR generally 200-1000 nm). The push towards thinner layers and the introduction of complicated new materials have challenged the sensitivity of such instrumentation. As a result, this has necessitated an effort to develop optical reflectometry equipment utilizing shorter wavelengths (below 200 nm), where greater sensitivity to subtle changes in material properties may be realized. One approach to performing such measurements is described in U.S. application Ser. No. 10/668,642, filed on Sep. 23, 2003, which discloses a system and method for a vacuum ultraviolet (VUV) reflectometer, the disclosure of which is incorporated herein by reference.

To obtain meaningful quantitative results from reflectometry data it is desirable to normalize or calibrate measured reflectance values in order to generate absolute reflectance spectra. At longer wavelengths in the DUV-NIR region this has traditionally been accomplished using a variety of techniques.

Due to the complexity of absolute reflectometer systems, commercial reflectometers generally measure reflected intensity, which is calibrated to a known absolute reflectance standard. In the DUV-NIR wavelength range, a silicon wafer (with native SiO2 layer) is typically used as the optical properties are well-known and the reflectance fairly stable over this wavelength range.

The precise calibration steps vary from instrument to instrument, but in essence the quantity usually measured is $$R = \frac{I_r}{I_0} \qquad \text{eq. 1}$$

where $I_r$ is the intensity reflected from the sample and measured by the detector, and $I_0$ is the incident intensity. $I_0$ is generally not known. In addition, $I_0$ will change over time due to environmental changes, drift in the optical system caused by environmental changes, and to drift of the intensity profile of the light source. At any given point in time, $I_0$ is determined by a calibration procedure:

$$I_0 = \frac{I_{cal}}{R_{cal}} \qquad \text{eq. 2}$$

where $I_{cal}$ is the measured intensity of the calibration standard, and $R_{cal}$ is the assumed reflectance of the calibration standard. If enough information about the calibration sample is known, e.g. optical properties, surface roughness, etc., then $R_{cal}$ can be generated using standard thin film models. Subsequent measurements are performed calibrated using this $I_0$ via eq. 1.

This procedure as usually implemented assumes that changes in $I_{cal}$ are due only to the environmental or lamp intensity changes mentioned above, and not due to changes to the calibration standard itself. In fact, variations in the calibration standard over time are generally not detectable using the above method, since such changes are simply "calibrated out". Obviously, the accuracy and stability of all subsequent reflectance measurements is highly dependent on the accuracy of the assumptions used to generate $R_{cal}$, as well as the stability of the calibration sample itself over time.

Some calibration techniques involve complicated optical arrangements that incorporate moving mirrors. Examples of such methods are provided in U.S. Pat. No. 4,368,983 (and references incorporated therein) which describes an apparatus and method to measure the absolute reflectivity of a sample using a multiple pass reflectometer.

While such methods offer a means of obtaining calibrated reflectance data, they generally suffer from the fact that they are time-consuming, involve considerable mechanical motion and can not easily be integrated into systems suitable for use in semiconductor manufacturing environments. Furthermore, many of these methods were designed for use in single wavelength reflectometers wherein a single wavelength detector is used in combination with a wavelength selecting pre-monochromator.

Ideally, it would be desirable to provide a technique by which broad-band reflectometry data could be simultaneously calibrated quickly and simply and in a manner that would lend itself suitable for use in semiconductor manufacturing environments.

One calibration approach is presented in U.S. Pat. No. RE 34,783 wherein a method is described that involves measuring the reflectance from a calibration sample whose absolute reflectance is well known, dividing the measured value by the absolute value to obtain a system efficiency coefficient and then, without changing the illumination or optics, measuring the reflectance of an unknown material and applying the coefficient to the measured value to obtain its absolute value.

In practice, single crystal silicon wafers are commonly employed as calibration samples since they are readily available, controllably manufactured and their optical properties in the DUV-NIR region have been well characterized. This approach works reasonably well at wavelengths above ~250 nm where the reflectance of single crystal silicon is both stable and predictable.

At shorter wavelengths (<250 nm) the reflectance of single crystal silicon wafers is neither stable nor predictable. Subtle variations in the thickness of the naturally (or "native") formed silicon dioxide layer present on the wafer can significantly influence the measured reflectance. Additionally, ultrathin layers of moisture and/or hydrocarbons are known to adsorb onto the surface further modifying the sample reflectance in this spectral region. As a result, it is generally not advisable to regard the reflectance of single crystal silicon wafers at wavelengths <250 nm as a "known" property.

One approach to overcoming this problem is presented in U.S. Pat. No. 5,798,837, which describes an optical measurement system that includes a reference ellipsometer and at least one non-contact optical measurement device, such as a reflectometer. The reference ellipsometer is used to determine an optical property of the calibration sample. The optical measurement device is then calibrated by comparing the measured optical property from the optical measurement device to the determined optical property from the reference ellipsometer.

Integration of a separate reference ellipsometer into an optical measurement system in order to calibrate the first optical measurement device is both complicated and expensive. Furthermore, the reference ellipsometer itself must be properly aligned and calibrated if it is to yield accurate results.

It follows that it would be highly desirable to develop a means of quickly and accurately calibrating broad-band data from an optical reflectometer operating at wavelengths <250 nm without the complication and expense associated with incorporating a second reference instrument into the system.

Additionally, it would be advantageous if this method specifically enabled the accurate calibration of reflectometry data at wavelengths encompassing the VUV spectral region, where small uncertainties in the properties of third party certified standards can result in substantial errors. It would be further desirable if this method was capable of independently determining the properties of such standards so as to reduce or altogether remove the need for their procurement and maintenance.

In addition to providing a technique to enable accurate calibration of reflectometry tools, it is desirable to provide a technique by which highly accurate thin film measurements may be performed. Optical reflectance measurements are used in a wide range of thin film applications. Ordinarily the absolute reflectance of a sample is recorded and subsequently analyzed using mathematical models in order to determine an assortment of physical properties.

Typically, the analysis is deemed complete when a quantitative indicator (generally referred to as the "goodness of fit" parameter) attains a specific value. Unfortunately, there are limits to the measurement accuracy that can be attained using conventional "goodness of fit" parameters. Hence, it follows that it would be desirable to develop a more sensitive measure of "goodness of fit" in order that higher levels of accuracy in thin film measurement may be obtained.

SUMMARY OF THE INVENTION

One embodiment of the current invention provides a means by which VUV reflectance data may be quickly and accurately calibrated. In one embodiment, the method enables simultaneous calibration of reflectance data covering a broad range of wavelengths. Additionally, the technique operates in a manner well suited for use in semiconductor manufacturing environments.

The method may be self-contained in that it may not require use of a second referencing instrument. It may provide a method by which calibration results may be autonomously verified such that use of third party certified standards will be reduced and/or altogether eliminated.

In one embodiment, the techniques include utilizing a standard (or "calibration") sample that allows for calibration in the wavelengths of interest even when the standard sample may exhibit significant reflectance variations at those wavelengths for subtle variations in the properties of the standard sample. Thus, calibration may be achieved even in cases where traditionally significant calibration error in regions of wavelengths that a user is interested in would be expected to be encountered. In this regard the technique takes advantage of the presence of a certain amount of calibration error that may be referred to as a calibration error function.

In another embodiment, the calibration process may include a technique that utilizes a first sample and a second sample. The first sample may include significant reflectance variation in the spectral region of interest as a function of sample property variations and the second sample may have a relatively featureless reflectance spectrum over the same spectral region. The first sample may be considered a standard or calibration sample and the second sample may be considered a reference sample. In one embodiment the spectral region may include the VUV spectral region.

In another embodiment a calibration technique is provided in which a standard or calibration sample may have relatively unknown properties with the exception that it may be assumed to have a significant calibration error function in the spectral regions of interest. Thus, the exact properties of the standard sample need not be known if it can be assumed that the standard sample exhibits sharp changes in reflectance for changes in the sample property.

In another embodiment of the current invention a technique by which highly accurate thin film measurements may be performed is provided. The method may provide mathematical fitting algorithms with a more sensitive "goodness of fit" indicator that is less susceptible to noise present in the raw data. The fitting routine may be a spectrally driven fitting routine rather than relying solely on an amplitude driven routine (which typically incorporates difference calculations). In such an embodiment, the measurements may be obtained by utilizing the presence of sharp, narrow spectral features.

In one embodiment, the measurements are obtained by a spectrally driven fitting routine that utilizes a ratio of an expected reflectance spectrum of the sample being measured to the actual reflectance spectrum of the sample being measured. Thus, rather than being based upon a difference between the expected and actual values, the techniques provided herein utilize a ratio of the values. The techniques are particularly useful in spectral regions that contain sharp spectral features, for example the sharp features that are often exhibited in the VUV region for thin film samples. Thus, a data convergent technique is provided that may beneficially utilize an absorption edge effect of the material is disclosed. In this manner sharp spectral features, for example resulting from either interference or absorption effects are advantageously utilized to better determine a data minimum that is indicative of an actual measurement value.

In another embodiment, the data reduction techniques may utilize a two step approach. In such an embodiment a low resolution step such as an amplitude driven fitting routine may be used to first provide a "coarse" measurement. Then a high resolution step such as a spectrally-driven fitting routine that advantageously utilizes the presence of sharp spectral features may be used to provide a "fine" measurement. In one embodiment, the low resolution step may obtain a rough measurement value by using a difference based technique as in a "Chi-square" merit function. The high resolution step may be a spectrally driven step that includes a ratio based technique in the region of interest initially identified by the low resolution technique.

In yet another embodiment, a reflectometer calibration technique is provided that may include the use of two calibration samples in the calibration process. Further, the technique allows for calibration even in the presence of variations between the actual and assumed properties of at least one or more of the calibration samples. In addition, the technique utilizes a ratio of the measurements from the first and second calibration samples to determine the actual properties of at least one of the calibration samples. The determined actual properties may then be utilized to assist calibration of the reflectometer.

In another example of the use of two calibration samples, a ratio of the intensity reflected from the first and second calibration samples may be utilized. The samples may exhibit relatively different reflective properties at the desired wavelengths. In such a technique the reflectance data of each sample may then be considered relatively decoupled from the other and actual properties of one or more of the calibration samples may be calculated. The determined actual properties may then be utilized to assist calibration of the reflectometer.

In another embodiment a method of calibrating a system that obtains reflectance data is provided. The method may include obtaining reflectance data from a first calibration sample and obtaining reflectance data from a second calibration sample, wherein exact properties of the at least one of the first and second calibration samples may vary from assumed properties of the calibration samples and wherein the reflective properties of the first and second calibration samples differ. The method may further include utilizing a ratio based upon the data obtained from the first calibration sample and the data obtained from the second calibration sample in order to assist in calibrating the system.

In still another embodiment a method of calibrating a reflectometer is disclosed. The method may include providing a first calibration sample and a second calibration sample, wherein the reflectance properties of the first calibration sample and the second calibration sample are different. The method further includes collecting a first set of data from the first calibration sample and collecting a second set of data from the second calibration sample. The method also includes utilizing a ratio of at least a portion of the first set of data and at least a portion of the second set of data to determine a property of at least one of the first and second calibration samples so that reflectance data from an unknown sample may be calibrated.

In another embodiment a method of calibrating a reflectometer which operates at wavelengths that include at least some wavelengths below deep ultra-violet (DUV) wavelengths is disclosed. The method may include providing a first calibration sample and a second calibration sample, wherein the reflectance properties of the first calibration sample and the second calibration sample are different. The method further includes collecting a first set of data from a first calibration sample, the first set of data including at least some intensity data collected for wavelengths below DUV wavelengths. The method also includes collecting a second set of data from the second calibration sample, the second set of data including at least some intensity data collected for wavelengths below DUV wavelengths. Further, the method may include utilizing a ratio based on the first set of data and the second set of data to determine a reflectance of at least one of the first calibration sample and the second calibration sample to assist in calibrating the reflectometer at wavelengths that include at least some DUV wavelengths.

In still another embodiment, a method of analyzing reflectometer data is disclosed. The method may include providing a first reflectometer sample and at least a second reflectometer sample, wherein the optical response properties of the first calibration sample and the second calibration sample are different. The method may further include collecting a first set of optical response data from the first reflectometer sample and collecting a second set of optical response data from the second reflectometer sample. The method further including determining at least one property of at least one of the first and second reflectometer samples by utilizing the first set and second set of optical response data in a manner independent of an incident reflectometer intensity that is utilized when collecting the first and second set of optical response data.

A further understanding of the nature of the advantages of the present invention may be realized following review of the following descriptions and associated drawings.

DESCRIPTION OF THE PREFERRED EMBODIMENTS

Figure 1:
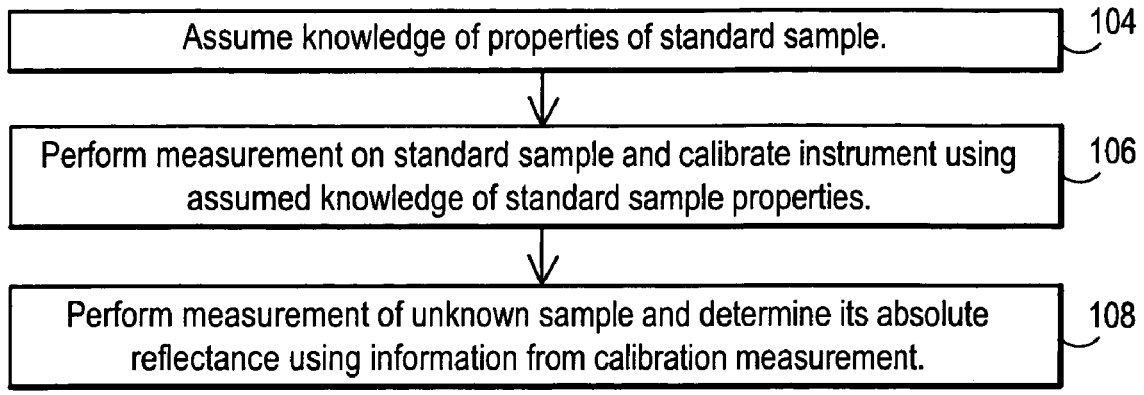
FIG. 1 illustrates a prior art calibration and measurement flowchart for a reflectometer.

The manner in which standard samples are typically used to calibrate reflectometers is generally presented in the flowchart 102 of FIG. 1. As is evident in the figure the first step 104 in the calibration process is to assume knowledge of the reflectance properties of the standard sample. With this information in hand, the intensity of light reflected from the sample as a function of wavelength can be recorded and the reflectometer calibrated in step 106. Subsequently, the reflectance of unknown samples may then be absolutely determined with the device in step 108.

Figure 2:
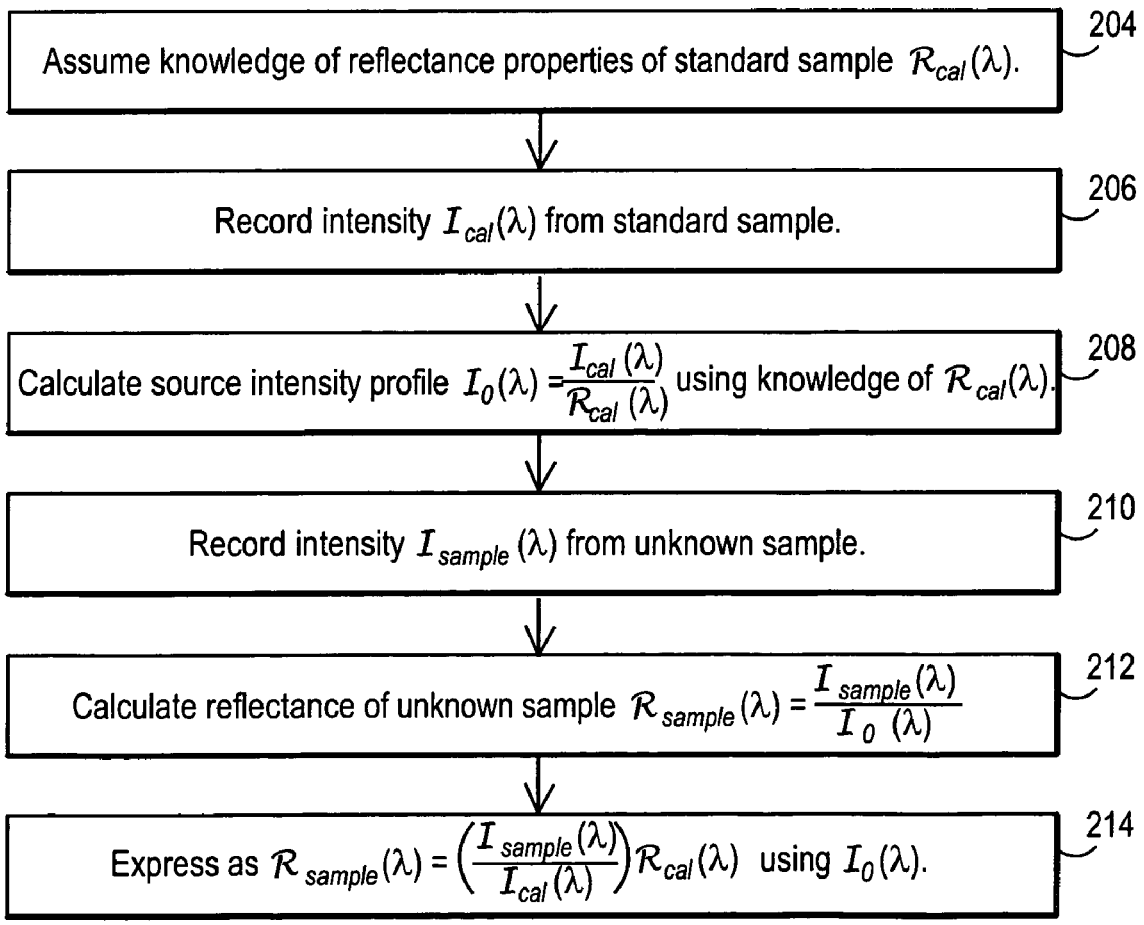
FIG. 2 illustrates a prior art detailed calibration and measurement flowchart for a reflectometer.

A more detailed description of this calibration procedure is outlined in the flowchart 202 of FIG. 2 wherein the mathematical relationships involved in calculating the absolute reflectance of an unknown sample are presented. FIG. 2 illustrates the flowchart 202 for the calibration procedure. In a first step 204, knowledge of reflectance properties of a standard sample is assumed. Then in step 206 the intensity from the standard sample is recorded. Next the source intensity profile is calculated in step 208 using knowledge of the assumed reflectance properties of the standard sample. In step 210, the intensity from an unknown sample is recorded. The reflectance of the unknown sample may then be calculated as shown in step 212. The reflectance of the unknown sample may then be expressed according to the equation of step 214. From examination of the final step of the process it is evident that the measured reflectance of an unknown sample is directly proportional to the assumed reflectance of the calibration sample. Hence, if the assumed reflectance is inaccurate it follows that the measured reflectance will also be inaccurate.

Single crystal silicon wafers have long been used as calibration standards for reflectometers operating in the DUV-NIR. They have proved a sensible choice as they are ubiquitous, controllably manufactured and optically well characterized in this spectral region. In practice the assumed reflectance properties for the silicon wafer are calculated using the Fresnel Equations and an assumed knowledge of the optical properties and thickness of the native silicon dioxide surface layer and the optical properties of the silicon itself.

When employed for the calibration of reflectometers operating at wavelengths longer than about 250 nm silicon wafers work well since the underlying assumptions regarding their physical properties are relatively insensitive to error in this wavelength region. In other words, errors in the assumed thickness of the native oxide layer on the surface of the wafer do not significantly influence the expected reflectance of the sample and hence negatively impact the accuracy of the calibration process.

Figure 3:
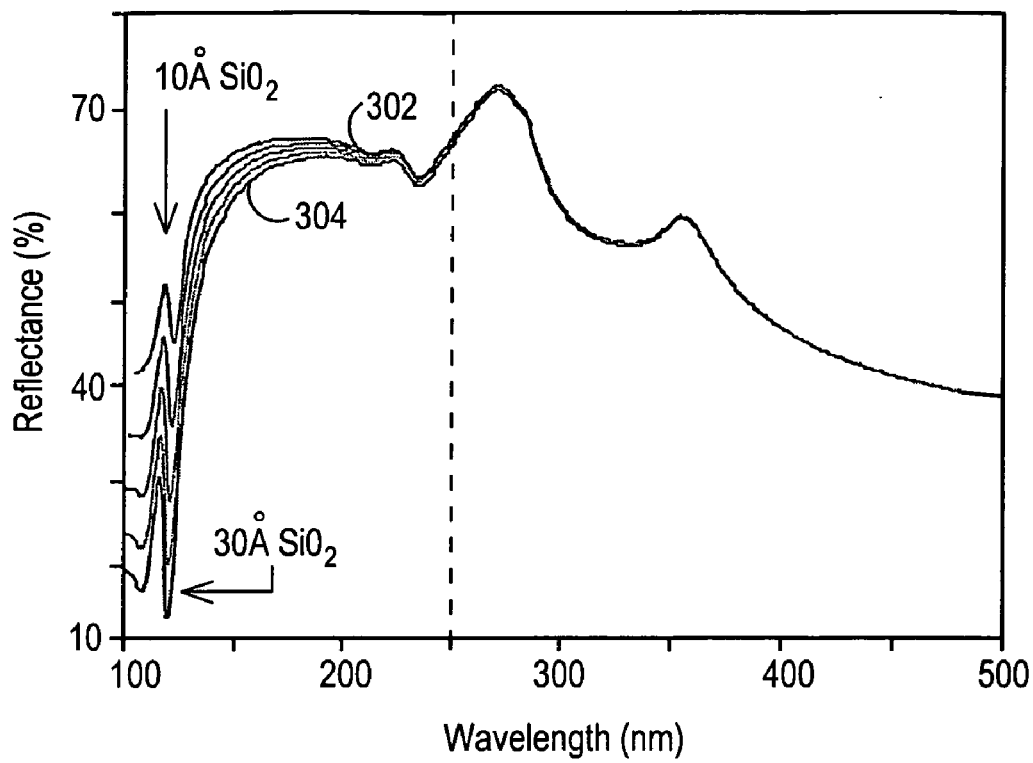
FIG. 3 illustrates reflectance spectra from ultra-thin SiO2/Si samples.

This point is further illustrated in FIG. 3 wherein calculated reflectance spectra for a series of $SiO_2$/Si samples with $SiO_2$ thicknesses ranging from 10 to 30 Å are presented. For example, reflectance spectrum 302 illustrates a Si sample having a 10 Å $SiO_2$ layer while reflectance spectrum 304 illustrates a Si sample having a 30 Å $SiO_2$ layer. While differences between the spectra are reasonably small above 250 nm, they become quite significant at shorter wavelengths. Hence, if the thickness of the native oxide layer is assumed to be 10 Å and is actually 20 Å then a considerable calibration error will be introduced at wavelengths lower than 250 nm.

Figure 4:
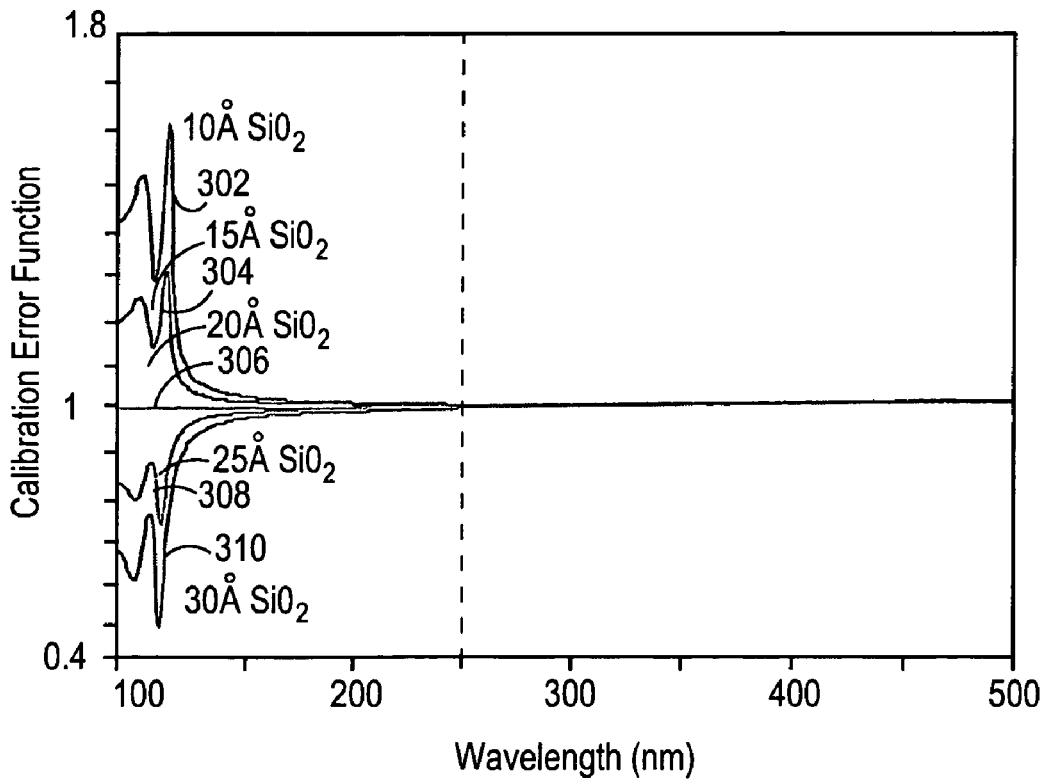
FIG. 4 illustrates calibration error spectra for a 20 Å SiO2/Si sample generated for a series of assumed thicknesses.

FIG. 4 better illustrates the effect of such errors. Plotted in this figure are a series of curves corresponding to the ratios of pairs of reflectance spectra. The first spectrum in each pair corresponds to that expected from a $SiO_2$/Si sample with an "assumed" native oxide thickness (ranging from 10 to 30 Å), while the second spectrum in each pair corresponds to a $SiO_2$/Si sample with an "actual" native oxide thickness of 20 Å. Thus, curve 302 of FIG. 4 corresponds to the ratio of the reflectance spectrum for an assumed native oxide thickness of 10 Å to the reflectance spectrum of a native oxide thickness of 20 Å. Similarly curve 304 of FIG. 4 corresponds to the ratio of the reflectance spectrum for an assumed native oxide thickness of 15 Å to the reflectance spectrum of a native oxide thickness of 20 Å. In a similar fashion curves 306, 308 and 310 illustrate the ratio of an assumed native oxide thickness of 20, 25, and 30 Å (respectively) to the reflectance spectrum of a native oxide thickness of 20 Å. In this sense the ratio may be considered essentially as a measure of calibration error, herein referred to as the calibration error function (CEF). The closer CEF is to unity, the lower the error associated with the calibration. In the case where the "assumed" thickness is equal to the "actual" thickness of 20 Å as shown by curve 306, the CEF is equal to one at all wavelengths and the calibration is perfectly accurate. In the situation where the "assumed" thickness is 25 Å (an error of just 5 Å) the CEF attains a value of greater than 1.3 at short wavelengths, while maintaining a value of less than 1.002 at wavelengths above 250 nm. This represents an error of greater than 30% in the VUV and less than ~0.2% at longer wavelengths. Hence, while silicon wafers may be readily used to calibrate reflectometers at wavelengths greater than 250 nm, they do not provide a practical means of accurately calibrating reflectometers in the VUV.

In addition, it is generally known that the native $SiO_2$/Si system will develop an ultra-thin (~1 nm or less) organic hydrocarbon layer in normal manufacturing or laboratory environments. In addition, organic material can build up on the surface of films during operation of a VUV tool. This type of contaminant layer may be removable by cleaning in acid or even using the VUV source itself. However, the fluctuating organic layer during tool use can cause significant fluctuation in the reflectance properties in the VUV region.

Another source of error is the buildup of a silicone-based contaminant on surfaces exposed to VUV radiation due to the presence of siloxane-based compounds in typical manufacturing environments. This "baked on" layer is harder to remove. Over time, this contaminant layer builds up on the surface of the native $SiO_2/Si$ standard sample, causing the absolute reflectance of the standard to decrease, especially in the VUV region. This means that a calibration procedure which always generates $R_{cal}$ assuming the native $SiO_2/Si$ structure will often yield incorrect results in the VUV.

These changes generally affect every measurement and have a significant impact on the reliability of VUV reflectance data. What is needed is a way to distinguish changes that occur in the calibration standard itself from changes in $I_0$ caused by system drift, and to correct the absolute calibration procedure when those changes occur.

Figure 5:
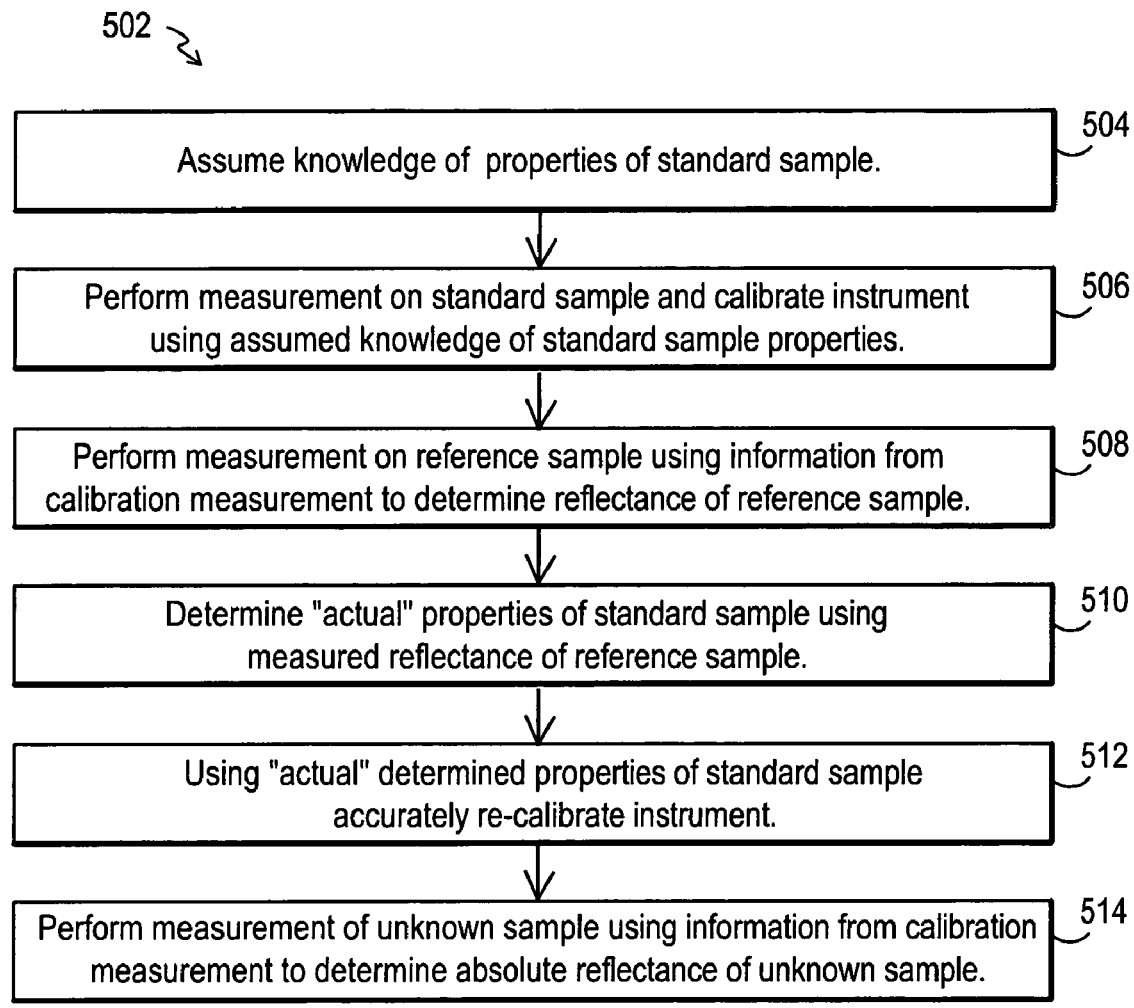
FIG. 5 illustrates an exemplary calibration and measurement flowchart according to one embodiment of the present invention.

An alternate approach to resolving these problems is afforded by an embodiment of the current invention. The flowchart 502 depicted in FIG. 5 provides a general overview of the steps involved in the process. As is evident from the figure the technique requires the use of two samples, a standard and a reference. The standard sample is chosen such that it is expected to exhibit a significant and spectrally sharp CEF over some spectral region. The reference sample, on the other hand, is selected such that it is expected to exhibit a relatively featureless reflectance spectrum over the same spectral region.

The first two steps 504 and 506 of the process are in effect identical to those described in the conventional method of FIG. 1. Namely, knowledge of the properties of the standard sample is assumed, following which the intensity of light reflected from the sample as a function of wavelength is recorded and used to calibrate the reflectometer. At this point the calibrated reflectometer is used to measure a reference sample and determine its reflectance as described in step 508. Once this has been accomplished, in step 510 the "actual" properties of the standard sample are determined through evaluation of the measured reflectance properties of the reference sample and the CEF. With knowledge of the "actual" properties of the standard sample in hand, the reflectometer can then be accurately re-calibrated in step 512, thereby removing imprecision resulting from errors associated with the "assumed" properties of the standard sample in the second step of the process. Once the instrument has been re-calibrated the absolute reflectance of unknown samples may be accurately determined as shown in step 514.

In one embodiment, the calibration techniques are dependent on the choice of the standard sample. As discussed earlier, it is desirable for the standard to exhibit a significant and spectrally sharp CEF spectrum over some spectral region of the reflectometer. To a great degree this capacity will be dictated by the optical nature of the sample. Specifically, the CEF signal generated by a standard sample is expected to increase in the vicinity of an optical absorption edge corresponding to one or more of the materials comprising it. In this spectral region small changes in the properties of the sample can generate significant changes in the reflected signal and hence a large CEF contribution. It follows that it is thus desirable that the reflectometer has sufficient spectral resolution to ensure sharp features of the CEF signal are detected and accounted for.

Figure 6:
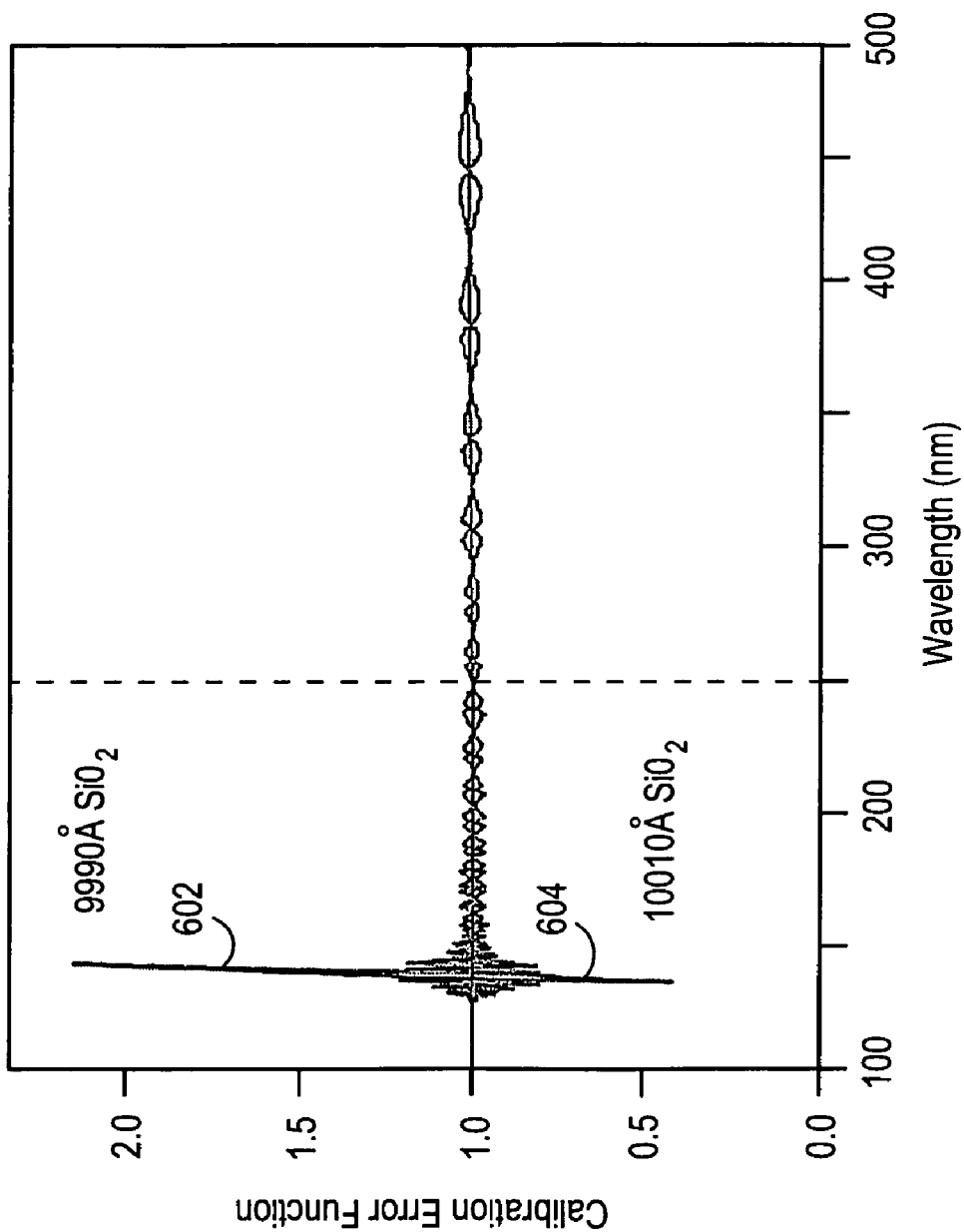
FIG. 6 illustrates calibration error spectra for a 10000 Å SiO2/Si sample generated for a series of assumed thicknesses.

In a preferred embodiment of the invention, designed to calibrate a VUV reflectometer, the standard sample is comprised of a relatively thick (~10000 Å) layer of $SiO_2$ deposited on a silicon substrate. FIG. 6 presents a CEF plot for such a standard, wherein the ratios of three pairs of reflectance spectra are plotted for "assumed" $SiO_2$ thicknesses of 9990, 10000 and 10010 Å. As is evident from the graph, the spectra 602 corresponding to the 9990 Å assumption and the spectra 604 corresponding to the 10010 Å assumption both exhibit substantial and spectrally sharp CEF features (in the case where the "assumed" thickness is equal to the "actual" thickness of 10000 Å the CEF is equal to one at all wavelengths). In fact, the data in the figure indicates that the 10 Å error (representing just 1 part in 1000) would introduce an inaccuracy of greater than 200% in the VUV reflectance results.

In contrast to the CEF plot for the 20 Å $SiO_2/Si$ sample presented in FIG. 4, wherein the CEF values at wavelengths longer than 250 nm displayed little in the way of error (owing to the fact that they all approached unity even when the assumed and actual thicknesses were not the same), the CEF values for the 10000 Å $SiO_2/Si$ sample plotted in FIG. 6 exhibit measurable error at virtually all wavelengths when the assumed and actual thickness are not the same. It is important to note, however, that the sharpest and most intense features in the CEF again occur in the VUV (a direct consequence of the presence of the $SiO_2$ absorption edge in this region).

While the 10000 Å $SiO_2/Si$ sample provides an exemplary standard for the purposes of the current invention, as a result of the significant CEF signal it generates for small errors in "assumed" thickness, it will be clear to one skilled in the art that many other samples may function equally as well. In general, any sample that produces a substantial CEF signal for small error in "assumed" thickness or some other assumed sample property may be employed.

As defined within the scope of this disclosure, the CEF is essentially a ratio of the "assumed" and "actual" reflectance spectra for a standard (or "calibration") sample. If the assumptions regarding the standard sample are completely accurate, the CEF assumes a value of one at all wavelengths. If instead the assumptions are to some extent flawed, the CEF will display values greater or less than one. The greater the inaccuracies in the assumptions, the greater the CEF values will deviate from unity.

While the CEF clearly provides a sensitive indicator of calibration accuracy it is not, itself, observable. One aspect to exploiting the CEF is therefore to use the reference sample to render the CEF features apparent. This follows since all measurements performed on samples following the initial calibration are in effect the product of the CEF and the "actual" reflectance spectrum of the sample under study. Hence if the reference sample, with its substantially smooth and featureless reflectance spectrum, is measured and if the CEF is not equal to unity then the intense sharp features in the CEF will be clearly evident in the reflectance spectrum recorded from the reference sample. Thus, even without prior intimate knowledge of the "actual" reflectance properties of the reference sample (other than that the reference sample is relatively featureless in the spectral region of interest) it is possible to readily evaluate the characteristics of the CEF and hence, gauge the accuracy of the initial assumptions regarding the properties of the standard sample.

Figure 7:
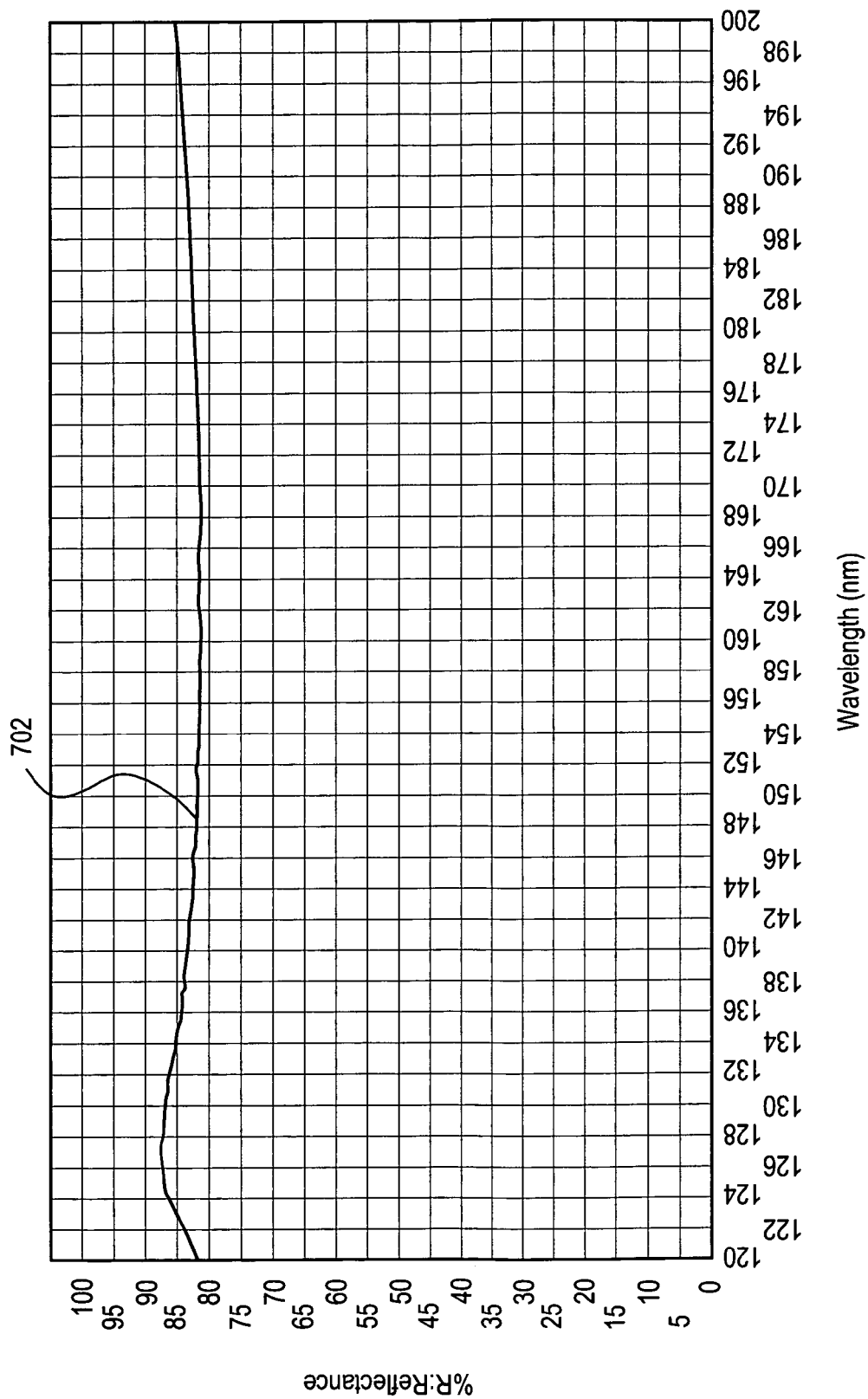
FIG. 7 illustrates a reflectance spectra for a broad-band VUV mirror (#1200) manufactured by Acton Research Corp.

While any sample with a substantially smooth and featureless reflectance spectrum may be employed as a reference sample a particularly well-suited choice may be a broad-band VUV mirror like the broad-band VUV mirror having coating #1200 manufactured by Acton Research Corporation of the United States. A typical reflectance spectrum 702 for this type of mirror is presented in FIG. 7. As is evident from the figure this broad-band mirror combines high reflectance throughout the entire VUV region with a largely featureless spectrum. It may be noted from FIG. 7 that the reference sample does not display sharp features in a spectral region such as the VUV where the standard sample may display a significant CEF. The sample used for a reference sample need not provide a consistent reflectance spectrum from sample to sample. For example, the same type of broad-band VUV mirror with the same coating from the same manufacturer may show a difference in absolute reflectance from mirror to mirror. However, if for any given mirror a relatively smooth and featureless reflectance spectrum is provided (at least in the spectral range of interest), then the mirror may be suitable for use as a reference sample. Furthermore, even if the reference sample (such as the mirror described above) exhibits absolute reflectance changes over time, the sample may still be suitable as a reference sample. Thus, the repeatability of the manufacturing of the reference sample and the changes in properties over time are not as significant as the sample's featureless properties in the desired spectral range.

It will be recognized by those in the art that one type of sample that is relatively featureless in the spectral region of interest such as the VUV is a silicon sample that has a native oxide on the sample. Such samples are relatively featureless when compared to a silicon sample with a thick oxide such as 1000 Å $SiO_2$/Si. Thus, as described herein in one alternative embodiment a standard sample may a 1000 Å $SiO_2$/Si sample and a reference sample may be a silicon sample with a native oxide layer.

Thus, a technique is provided that includes utilizing a standard sample that allows for calibration in the wavelengths of interest even when the standard sample may exhibit significant reflectance variations at those wavelengths for subtle variations in the properties of the standard sample. Calibration may be achieved even in cases where traditionally significant calibration error in regions of wavelengths that a user is interested in would be expected to be encountered. In this regard the technique takes advantage of the presence of a certain amount of calibration error that may be referred to as a calibration error function.

The calibration process may thus include a technique that utilizes a first sample and a second sample. The first sample may include significant reflectance variation in the spectral region of interest as a function of sample property variations and the second sample may have a relatively featureless reflectance spectrum over the same spectral region. The first sample may be considered a standard or calibration sample and the second sample may be considered a reference sample. By first calibrating the system using a standard sample and then measuring a reference sample, any sharp changes in the reflectivity observed from the reference sample may be assumed to be a function of the inaccuracies in the assumptions regarding the calibration sample. With this knowledge, the system may then be recalibrated.

Further, the calibration technique may utilize a standard sample that may have relatively unknown properties with the exception that it may be assumed to have a significant calibration error function in the spectral regions of interest. Thus, the exact properties of the standard sample need not be known if it can be assumed that the standard sample exhibits sharp changes in reflectance for changes in the sample property.

Before the reference sample measurement can be used to evaluate the results of the calibration process it is desirable to mathematically construct a means of quantifiably assessing the CEF in light of its coupling with the reference sample reflectance spectrum. In one embodiment of the invention this may be generally accomplished in the following manner.

First, the derivative of the measured reflectance spectrum is calculated. This acts to reduce the coupling between the CEF and the "actual" reflectance spectrum of the reference sample and places greater emphasis on "sharp" reflectance structures (likely contributed by the CEF) than on slowly changing features (expected from the reference sample). Next, the absolute value of the derivative is calculated and the resulting function integrated. Taking the absolute value of the derivative prior to integration is necessary in order to constructively capture both positive and negative values of the function and to avoid canceling out contributions to the derivative arising from the reference sample reflectance spectrum. With the integration complete it is possible to quantitatively evaluate the results of the initial calibration procedure.

In this manner the integrated value can be fed back to an algorithm that iteratively adjusts the initial assumptions regarding the properties of the standard sample, re-calculates the CEF and re-determines the integrated value in an effort to minimize its value. When the minimum has been achieved the "actual" properties of the standard sample, and hence its "actual" reflectance have been determined. At this point the reflectometer can be accurately calibrated and measurements on unknown samples performed.

Figure 8:
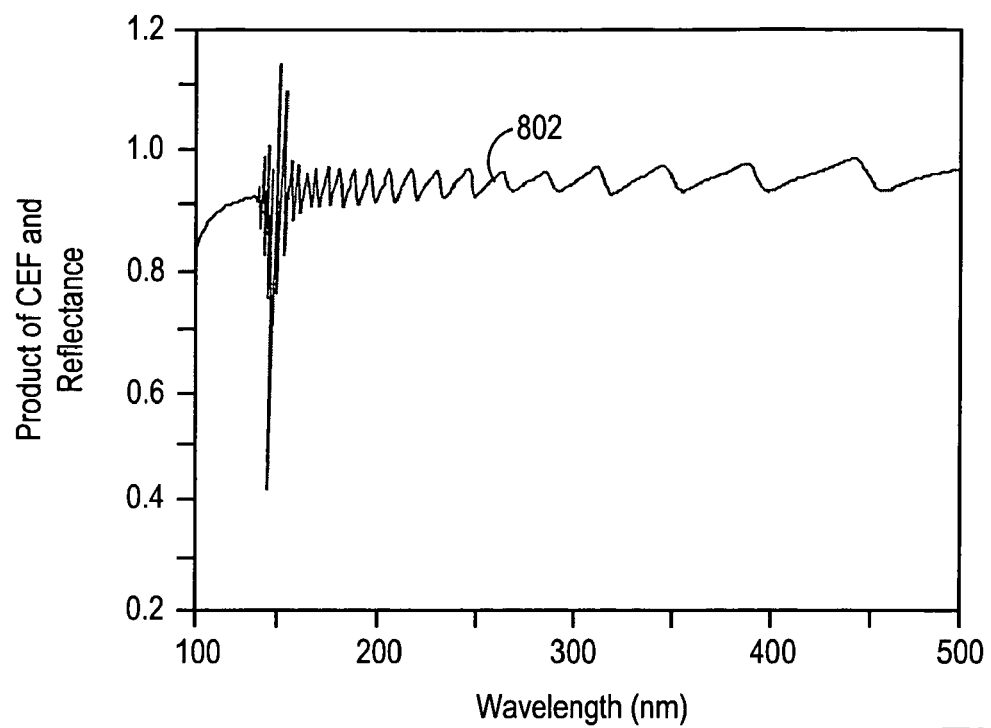
FIG. 8 illustrates a product of a reference sample reflectance spectrum and a calibration error function for a 10000 Å SiO2/Si sample obtained from the measurement of an arbitrary reference sample.

A further understanding of the steps involved in this method may be realized following a review of the data presented in FIGS. 8-11. FIG. 8 presents the results of a measurement performed on an appropriate reference sample following calibration with a 10000 Å $SiO_2$/Si standard sample using an "assumed" thickness of 10010 Å. The sharp structure evident in the measured spectrum of the reference sample (adjusted for the calibration) is a consequence of the 10 Å error introduced during the calibration process. Signal 802 shown in FIG. 8 is a measured spectrum obtained from the reference sample. This signal is a result of the product of the reflectance of the reference sample and the CEF spectrum resulting from the inaccurate calibration. At this point in the process, the CEF and reference sample reflectance signals are essentially coupled, and as is evident exist largely at shorter wavelengths in the VUV. In the present example, this occurs because the CEF signal was largely present in the VUV region and the reference reflectance was substantially featureless in this same region.

Figure 9:
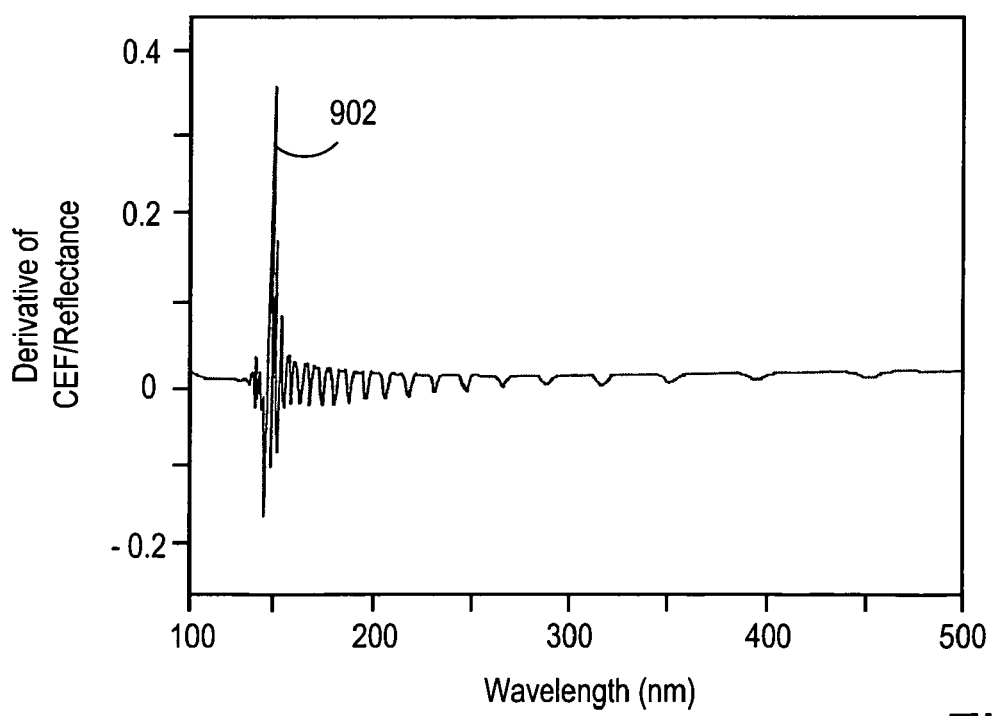
FIG. 9 illustrates a derivative of a calibration error function for a 10000 Å SiO2/Si sample generated for an assumed thickness of 10010 Å.

The derivative of this spectrum is presented in FIG. 9. Not surprisingly, the bulk of the CEF/reference reflectance product derivative signal 902 still resides in the VUV region of the spectrum. The absolute value of the trace is then calculated prior to integration, which ultimately yields a quantitative measure of calibration accuracy. This integrated sum is then returned to an iterative routine that adjusts the "assumed" thickness of the standard sample and recalculates the CEF/reference reflectance product integral until its value is minimized.

Figure 10:
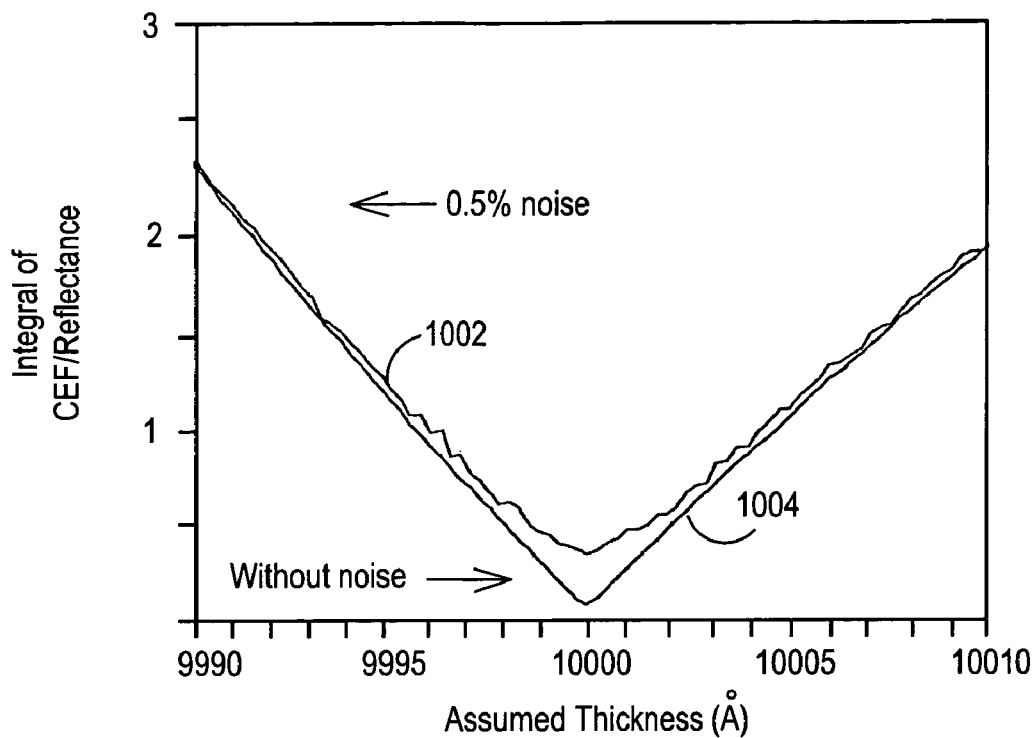
FIG. 10 illustrates a sensitivity plot calculated using a calibration error function integral for a 10000 Å SiO2/Si standard sample.
Figure 11:
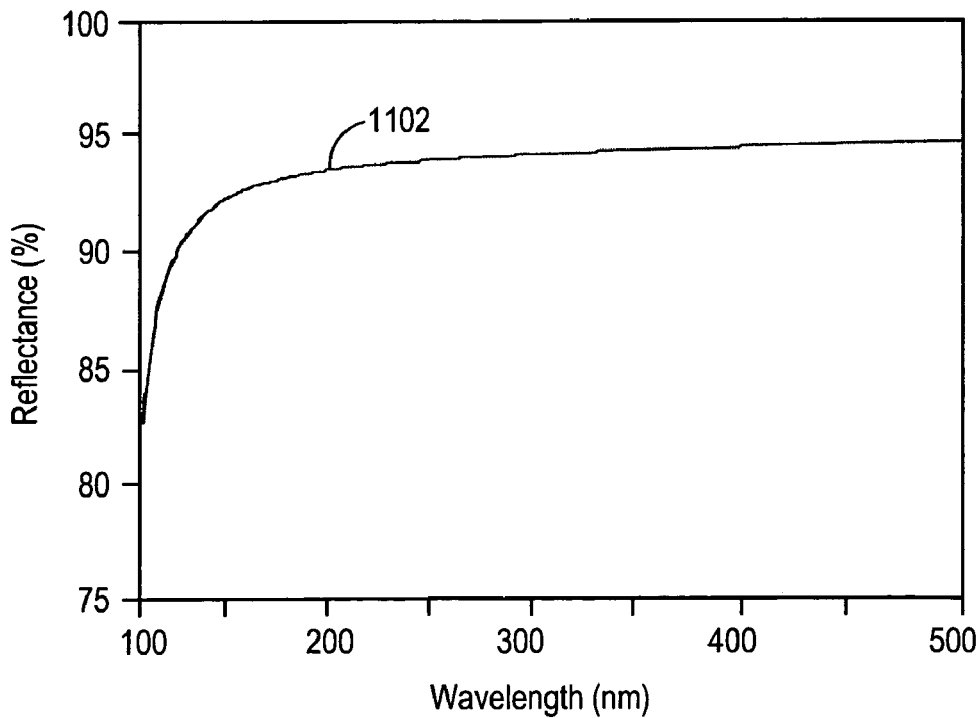
FIG. 11 illustrates a reflectance of a reference sample used in a calibration routine.

Values of the CEF/reference reflectance product integral as a function of "assumed" thickness are presented in the sensitivity plot of FIG. 10 for the 10000 Å $SiO_2$/Si standard sample with and without noise added to the system. Plot 1002 illustrates the values of the CEF/reference reflectance product integral including the presence of a 0.5% noise component while plot 1004 shows the data without noise. As is evident from examination of the data, the integral is extremely sensitive to small errors in the "assumed" thickness of the $SiO_2$ layer, even in the presence of a 0.5% noise component in the raw reflectance data. Needless to say, the minimum value of the CEF/reference reflectance product integral is achieved when the "assumed" thickness value matches the "actual" thickness of the standard sample. Following completion of the iterative process the "actual" properties of the standard sample are determined and the instrument is accurately calibrated. At this point in time the CEF function assumes a value of unity at all wavelengths and subsequent measurement of the reference sample yields its true reflectance spectrum 1102, as illustrated in FIG. 11.

Figure 12:
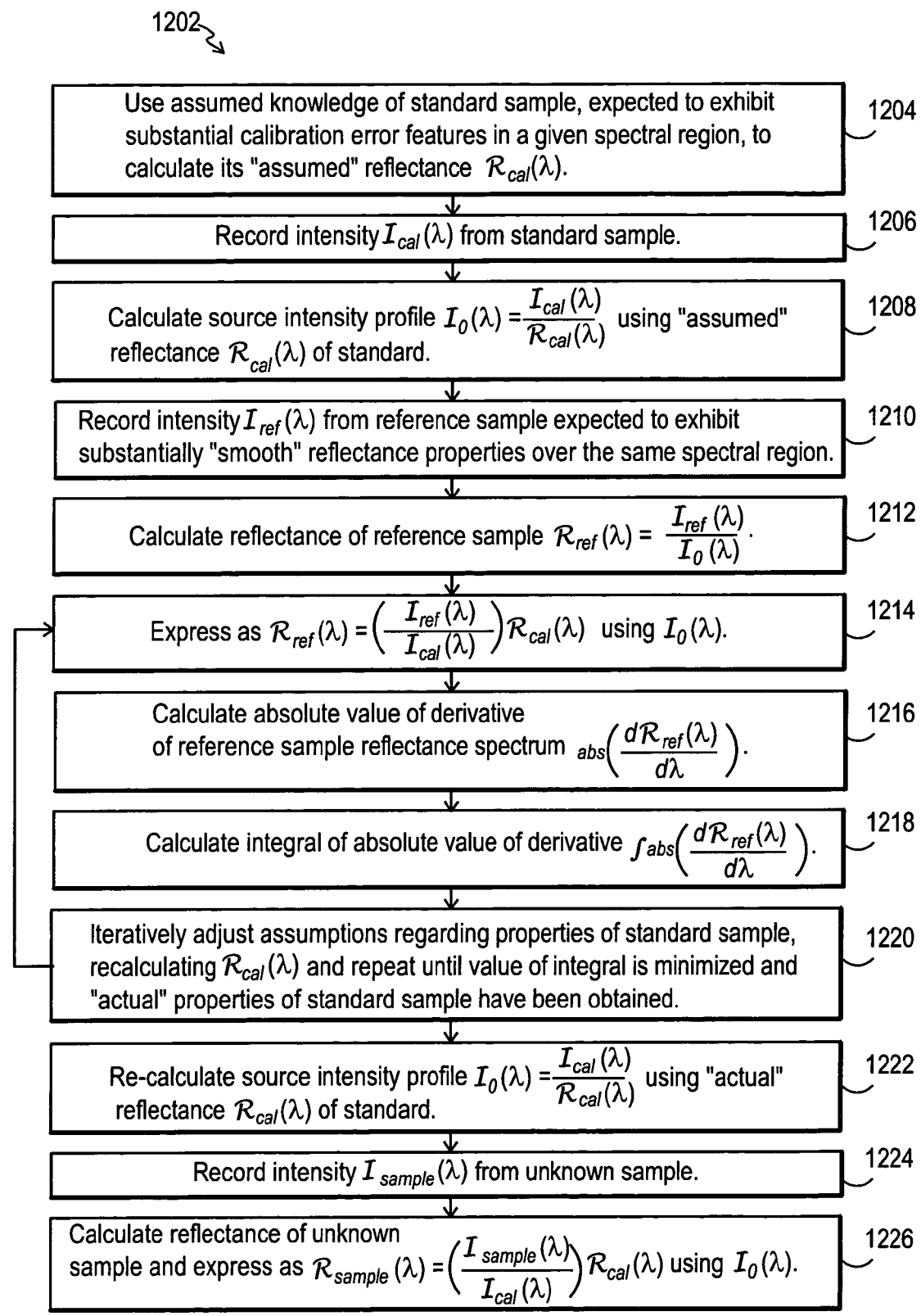
FIG. 12 illustrates an exemplary detailed calibration and measurement flowchart according to one embodiment of the present invention.

An exemplary and detailed description of this calibration procedure is outlined in the flowchart 1202 of FIG. 12 wherein the mathematical relationships involved in calculating the absolute reflectance of an unknown sample are presented. As shown in FIG. 12 step 1204, first the assumed knowledge of a standard sample, expected to exhibit substantial calibration error features in a given spectral region is used to calculate the assumed reflectance of the standard sample. In step 1206 the intensity from the standard sample is recorded. In step 1208, the source intensity profile is calculated using the assumed reflectance of the standard sample. The intensity from the reference sample that is expected to exhibit substantially smooth reflectance properties over the same spectral region is then recorded in step 1210. Next, in step 1212 the reflectance of the reference sample is calculated. The reflectance of the reference sample may be then expressed according to the equation of step 1214. The absolute value of the derivative of the reference sample reflectance spectrum may then be calculated in step 1216. The integral of the absolute value of the derivative is then calculated in step 1218. Next, in step 1220 an iterative adjustment of the assumptions regarding the properties of the standard sample is performed and the assumed reflectance of the standard is recalculated. Control is returned to step 1214 from step 1220 until the value of the integral is minimized and the actual properties of the standard sample are thus obtained at which point the process proceeds from step 1220 to step 1222. In step 1222 the source intensity profile is re-calculated using the actual reflectance of the standard. The intensity of an unknown sample is then recorded in step 1224. Finally, the reflectance of the unknown sample is calculated and expressed according to the equation of step 1226.

It will be recognized by those skilled in the art that many other methods exist for quantifying the CEF signal in such a manner as to render it useful for feedback to an iterative routine designed to minimize its value through adjustments in the "assumed" properties of the standard sample. In addition, while the above discussions have regarded the thickness of the standard sample as being the "assumed" property to be accurately determined during the calibration process, it will be further apparent to those skilled in the art that many other properties of the standard sample could also be treated as "assumed" properties and determined in the same manner. Such properties could include, but are not limited to, complex refractive index, composition, porosity and surface or interface roughness. These properties may be determined independently, or in some instances simultaneously along with other properties during the calibration procedure.

In certain circumstances additional mathematical steps may be performed to enhance the performance of the calibration routine. In the presence of significant noise in the measured reflectance data recorded from the reference sample it may be advantageous to filter the raw data prior to or after taking its derivative. While many appropriate smoothing filters exist in the prior art, the Savitzky-Golay filter is particularly well-suited to this application as it generally preserves the width and position of spectral features in the raw data. Additionally, in some situations it may prove beneficial to limit the range of wavelengths over which the integration is performed in order to further emphasize the contribution of the CEF signal.

Figure 12A:
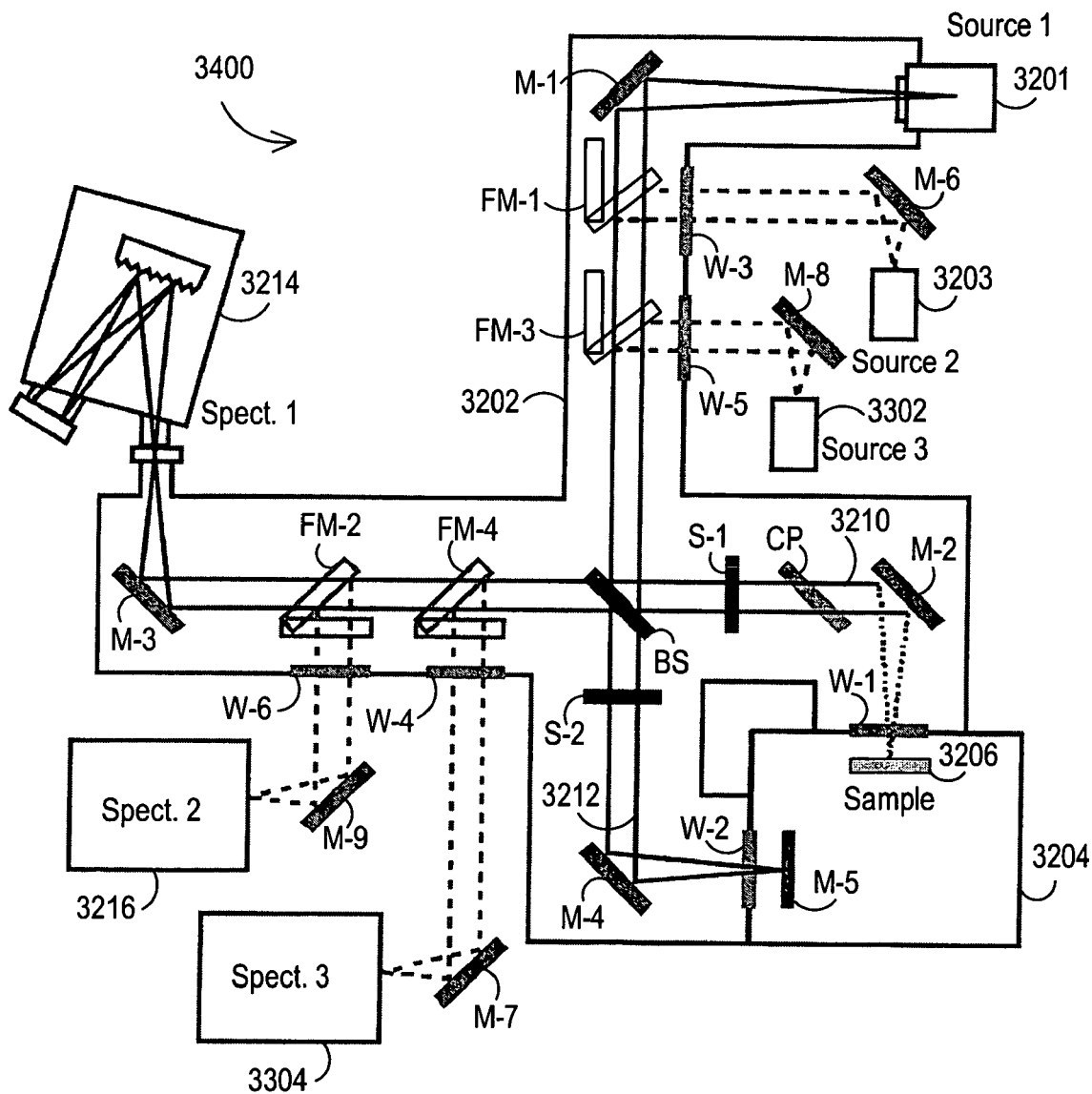
FIG. 12A illustrates an exemplary reflectometer system which may utilize the calibration concepts of the present invention.

It will be clear to those skilled in the art that the present invention readily lends itself to many modes of implementation. A particularly advantageous approach would be to integrate the reference sample into the reflectometer such that it could be effortlessly utilized. This approach is described in detail in U.S. application Ser. No. 10/668,644, filed on Sep. 23, 2003, which discloses a vacuum ultraviolet referencing reflectometer and in U.S. application Ser. No. 10/909,126 filed Jul. 30, 2004, the disclosures of which are incorporated herein by reference. An example of the use of the calibration techniques provided herein in combination with the systems described in the aforementioned prior filed U.S. Applications is illustrated in FIG. 12A. FIG. 12A provides a broadband reflectometer system 3400 as described in more detail with regard to FIG. 34 in U.S. application Ser. No. 10/909,126 filed Jul. 30, 2004. The system 3400 may optionally include multiple sources 3201, 3203, and 3302 and corresponding multiple spectrometers 3214, 3216, and 3304. Flip-in mirrors FM-1 through FM-4 and corresponding windows W-3 through W-6 may be utilized to select the various sources and spectrometers. Mirrors M-1 through M-5 are utilized to direct the beams as shown. A sample 3206 may be located in a sample beam 3210. A reference beam 3212 is also provided. A beam splitter BS is provided and shutters S-1 and S-2 select which of the beams is being utilized. The various optics and samples may be included in environmentally sealed chambers 3202 and 3204 such that measurements in the VUV bandwidth may be obtained.

As shown in FIG. 12A, a sample beam (or channel) 3210 is provided for obtaining measurements from a sample 3206. A reference beam (or channel) 3212 is provided for referencing the system. Generally, the reference beam is configured to provide a mechanism that is indicative of environmental or other system conditions. The reference beam may be configured to provide a beam path that is similar in beam length and environmental conditions as the sample beam, however, the reference beam does not encounter the sample 3206. In operation with the calibration techniques described herein, the standard sample may be placed at the sample 3206 location of FIG. 12A. A separate reference sample need not be placed at the sample 3206 location however (although such a use of a separate reference sample placed at the sample 3206 location may be utilized). Rather, the entire reference beam 3212 path may be construed as the "reference sample." For example, the cumulative effects of the beam splitter BS, mirror M-4, window W-2, and mirror M-5 (i.e. the elements that are different between the sample and reference paths) may be construed as together forming the "reference sample." Such use of an entire beam path for the reference sample is generally available if the combined effect of the optical elements provides a relatively smooth featureless reflectance spectrum in the spectral range of interest. It will be recognized that many other methods of utilizing the calibration techniques will be apparent to one skilled in the art and the calibration techniques described herein are not limited to the mechanical configurations referred to herein. Though not shown, the reflectometer system 3400 may include a processor, computer, other electronics, and/or software for calibrating the system according to the calibration techniques provided herein. The processor, computer, other electronics, and/or software may be constructed integral with the reflectometer optical hardware or may be a separate stand alone unit that together with the reflectometer optical hardware forms a reflectometer system configured to allow for calibration.

There are many advantages afforded by the current invention. One such advantage is that it provides a technique by which VUV reflectometry data may be accurately calibrated in light of the fact that uncertainties associated with commercially available thin film standard samples may be too large to enable accurate calibration using conventional methods. As a result, it may altogether eliminate the need for reflectometer tool users to purchase, maintain and recalibrate expensive standard samples.

Furthermore, the current invention allows one to achieve highly accurate calibration results without prior knowledge of the exact properties of either the standard or reference samples. This capability is particularly useful since virtually all samples can be expected to undergo subtle changes in their properties as a function of time, as a result of either natural growth mechanisms or contamination.

While particularly well-suited to the purpose of calibrating VUV reflectometry data, the present invention may also be used to calibrate reflectometry data from other spectral regions. In such instances it may be advantageous to employ the use of other standard samples which could be expected to generate substantial CEF signals in the spectral region of interest.

A further advantage of the invention is that it does not require use of a secondary reference instrument, thereby greatly reducing system cost and complexity.

Once reflectance data has been recorded from a calibrated reflectometer it is typically sent to a processor unit where it is subsequently reduced via analytical algorithms. These algorithms generally relate optical data, such as reflectance, to other properties of the sample, which can then be measured and/or monitored like film thickness, complex refractive index, composition, porosity, surface or interface roughness, etc.

Data reduction is generally accomplished using some form of the Fresnel Equations in combination with one or more models to describe the optical properties of the materials comprising the sample. Regardless of the specific model used in the reduction of the data set, the greater goal is generally to use a mathematical expression to describe the measured data such that certain parameters, relating to the properties of the samples (as discussed above), can be obtained through an iterative optimization process. That is, the measured data set is compared to one calculated using an expression that depends on a set of parameters relating to the nature of the sample. The discrepancy between the measured and calculated data sets is minimized by iteratively adjusting the values of the parameters until such time as adequate agreement between the two data sets is achieved. This discrepancy is usually quantified in terms of a "goodness of fit" (GOF) parameter.

Numerous mathematical expressions for calculating GOF exist in the prior art. Most of these techniques are to some degree based on a determination of the difference between the measured and calculated spectra. While these methods are generally applicable and do a reasonable job of locating the general region of the absolute minimum in parameter space, they often exhibit shortcomings upon convergence at that minimum, particularly in the presence of increasing levels of noise in the measured data.

Figure 13:
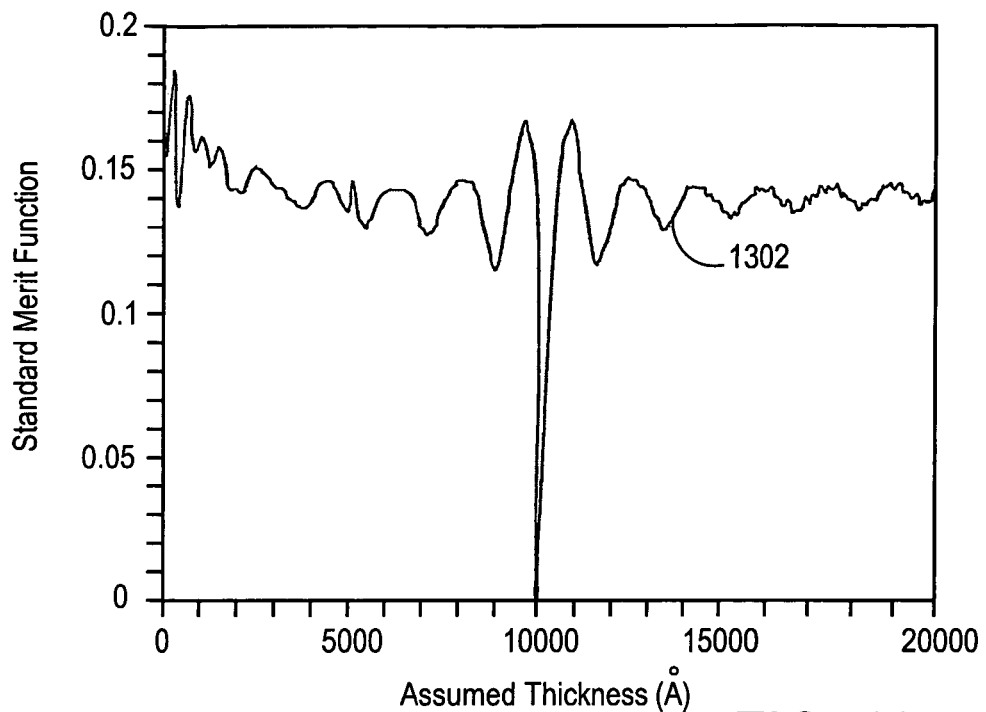
FIG. 13 illustrates the sensitivity plot calculated using a standard prior art merit function for a 10000 Å SiO2/Si sample.

FIG. 13 presents a sensitivity plot 1302 for a prior art GOF expression (known to those skilled in the art as the "Chi-square" merit function) as calculated for a 10000 Å $SiO_2$/Si test sample. As is evident this standard merit function provides an effective means of locating the general region of the "actual" thickness of the film, as it exhibits a relatively smooth line shape with a well-defined minimum. On closer examination, however, the sensitivity of the function is seen to degrade significantly in the immediate vicinity of the minimum. This point is better illustrated in FIG. 14, which presents an expanded view 1402 of the sensitivity plot 1302 of FIG. 13 in the presence of 1% noise in the measured reflectance data.

Figure 14:
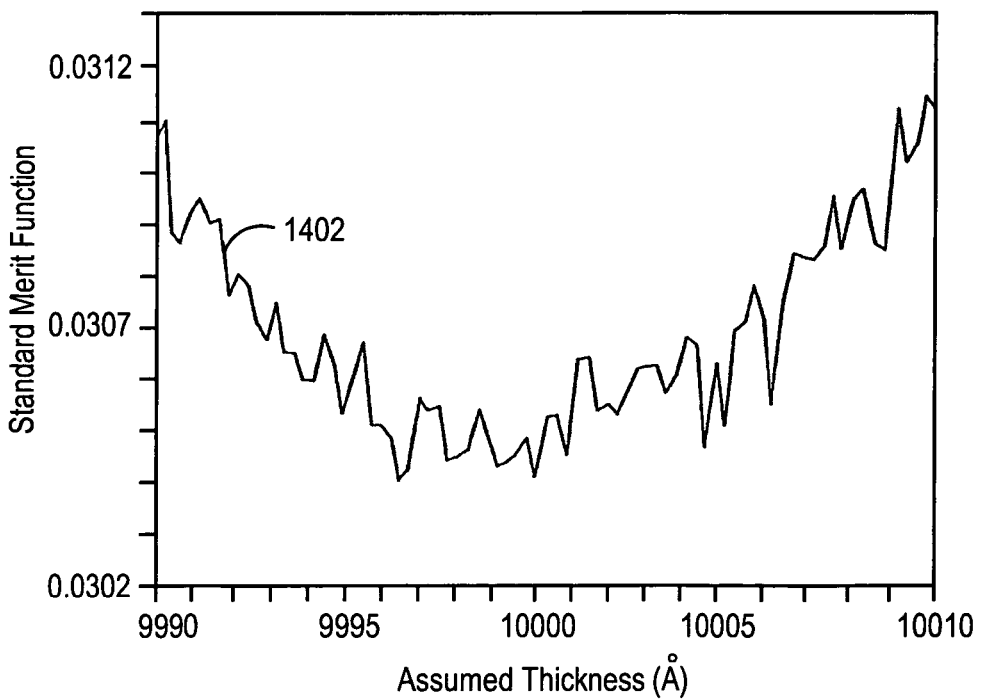
FIG. 14 illustrates an expanded sensitivity plot calculated using a standard prior art merit function for a 10000 Å SiO2/Si sample in the presence of 1% noise on the measured reflectance data.

As is evident upon examination of the data in FIG. 14 the 1% noise resident in the raw reflectance data significantly reduces the ability of the merit function to enable the minimization routine to converge upon the "actual" thickness of the test sample. Hence, it would be desirable to develop a superior method of determining the "actual" thickness once the routine has located the general vicinity of the solution.

Another preferred embodiment of the present invention provides this capability. Namely, it provides a highly sensitive measure of convergence that can be used in combination with an appropriate minimization routine to efficiently reduce measured reflectance data, thus yielding results exhibiting a higher level of accuracy then attainable using conventional techniques alone. While designed to be used in conjunction with traditional merit functions, the current invention may in some instances altogether supplant the use of such methods.

Figure 15:
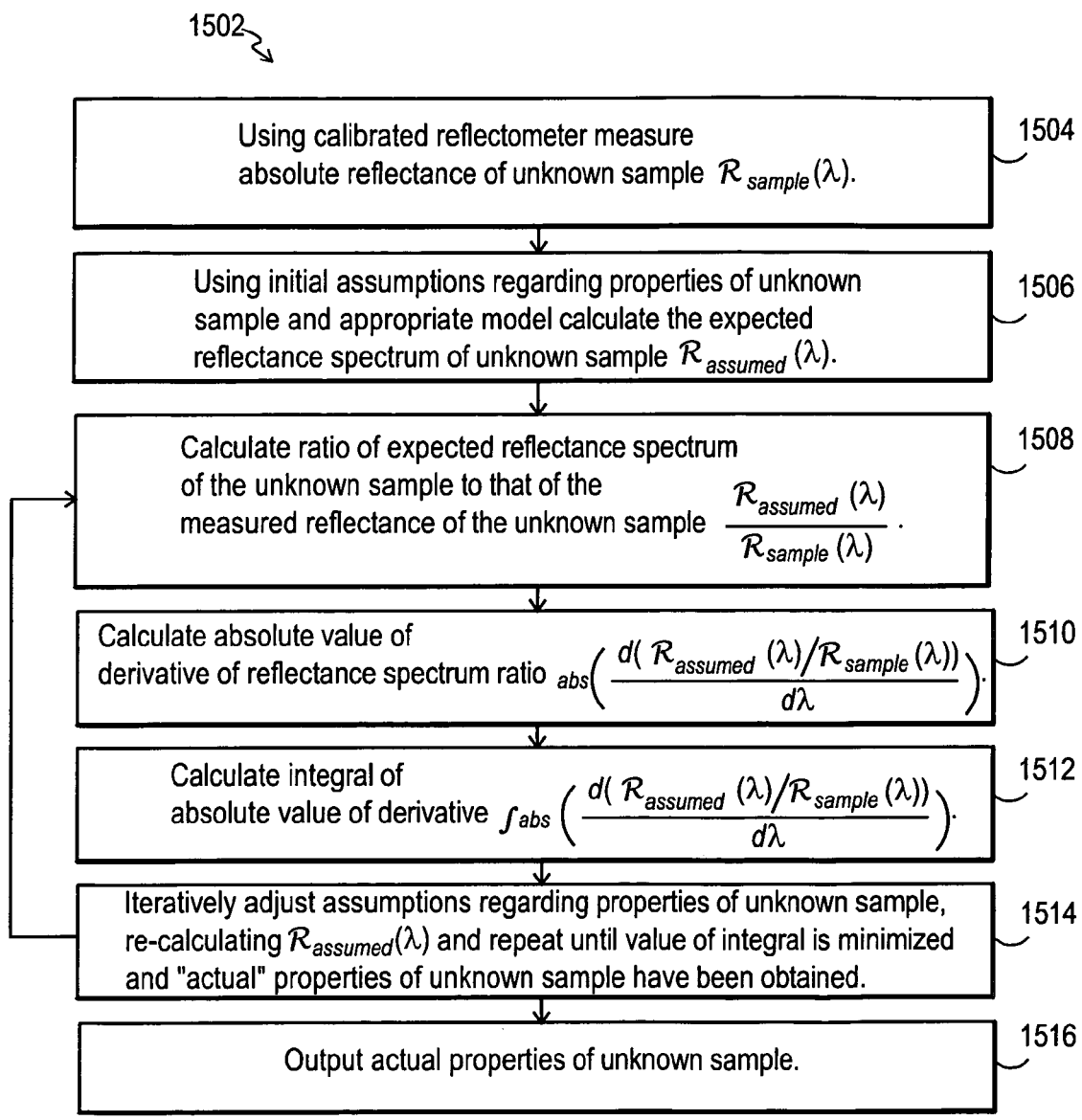
FIG. 15 illustrates an exemplary detailed measurement flowchart according to one embodiment of the present invention.

A general overview of one embodiment of the data reduction techniques described herein is presented in the flowchart 1502 of FIG. 15, wherein the mathematical relationships involved in an iterative data fitting routine associated with the measurement of an unknown sample using a reflectometer are presented. The first step 1504 in the process is to obtain the absolute reflectance spectrum of the unknown sample using an accurately calibrated reflectometer. Once this spectrum has been recorded the initial assumptions regarding the physical properties of the sample are used to calculate the "expected" reflectance properties of the sample in step 1506. With these two spectra in hand the ratio of the "expected" to "measured" spectra is determined as shown in the equation of step 1508.

This ratio, termed herein as the measurement error function (MEF), is similar in nature to the CEF discussed earlier. While both functions relate the ratio of "assumed" to "actual" data sets, the MEF is somewhat simpler to evaluate as it is not coupled with the reflectance of the reference sample. That is, during minimization the CEF is evaluated through examination of the reference sample reflectance spectrum, while the MEF is evaluated through examination of the reflectance of the unknown sample itself.

Before the MEF (or reflectance spectrum ratio) can be used to evaluate the results of the minimization routine a suitable merit function must again be constructed. Following the approach undertaken with the CEF earlier, the next step in the flowchart 1502 is to calculate the absolute value of the derivative of the MEF as shown in step 1510. This acts to accentuate sharp spectral features in the MEF, resulting largely from wavelengths in the vicinity of the absorption edge for one or more materials comprising the unknown sample. At this point the absolute value of the derivative is calculated and then the resulting function is integrated as shown in step 1512. As before, taking the absolute value of the derivative prior to integration is desirable in order to constructively capture both positive and negative values. Once the integration is complete it is possible to quantitatively evaluate the results of the reduction process. More particularly, an iterative process of adjusting assumptions regarding properties of the unknown sample and recalculating the expected reflectance spectrum of the unknown sample may occur as shown in step 1514. After the recalculation of the expected reflectance spectrum, control passes again to step 1508 and steps 1508-1514 are repeated until a value of the integral is minimized at which point the actual properties of the unknown sample are determined to have been obtained and control is passed to step 1516 where the actual properties of the unknown sample are provided as an output.

It is noted that this technique is insensitive to fixed offsets between the "assumed" and "measured" reflectance spectra. That is, it can not be effectively used to reduce long wavelength reflectometry data collected from samples comprised of very thin films (i.e. thin enough so as not to give rise to significant interference effects) since such data sets are unlikely to contain sharp spectral features that are required by this method. Fortunately, in the VUV region virtually all thin film samples exhibit some form of sharp structure in their reflectance spectra, resulting from either interference or absorption effects.

Figure 16:
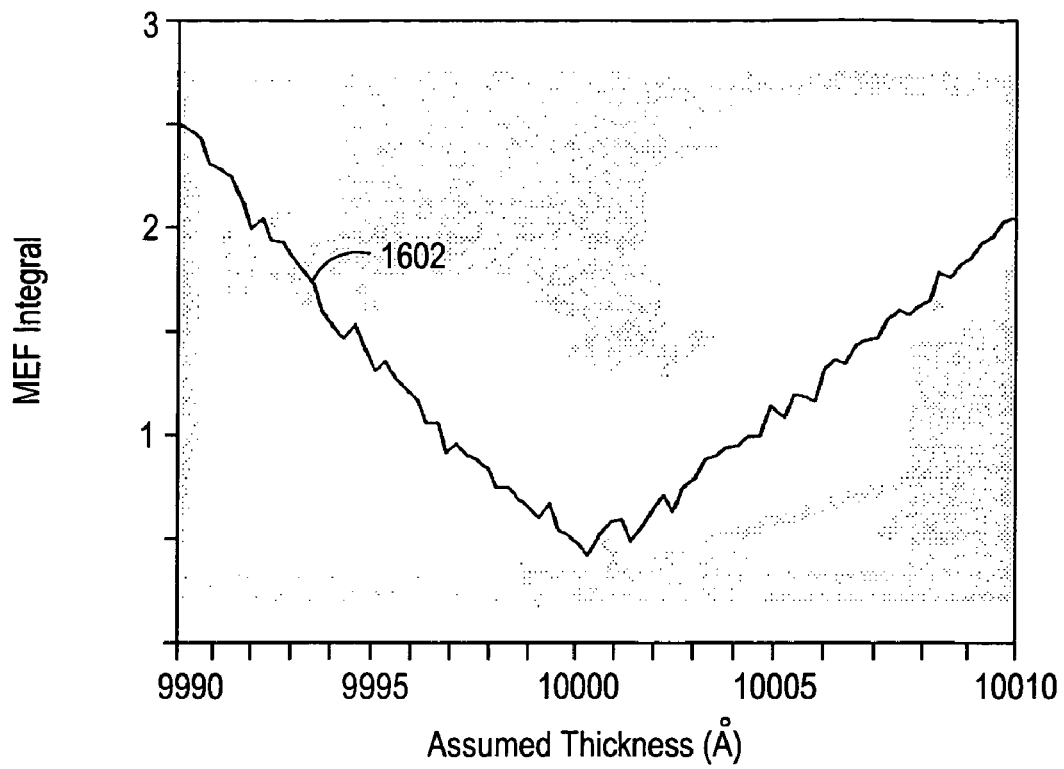
FIG. 16 illustrates an expanded sensitivity plot calculated using an MEF integral for a 10000 Å SiO2/Si sample in the presence of 1% noise on the measured reflectance data.

To better demonstrate the superior performance of this approach, relative to that of the conventional Chi-square method, FIG. 16 presents an expanded sensitivity plot 1602 calculated using an embodiment of the current invention for the same 10000 Å SiO$_2$/Si test sample of FIG. 14. Comparing the results in these two figures it is shown that the present invention is less affected by the 1% noise level present in the raw reflectance data, than is the Chi-square method. This establishes that the current invention provides the optimization routine with a more effective measure of the fit minimum and hence, the "actual"thickness of the film. This improved performance demonstrates that at least when the "assumed" thickness value is in the general vicinity of the "actual" thickness the current invention is capable of achieving a more accurate and repeatable result than is possible using conventional methods.

Figure 17:
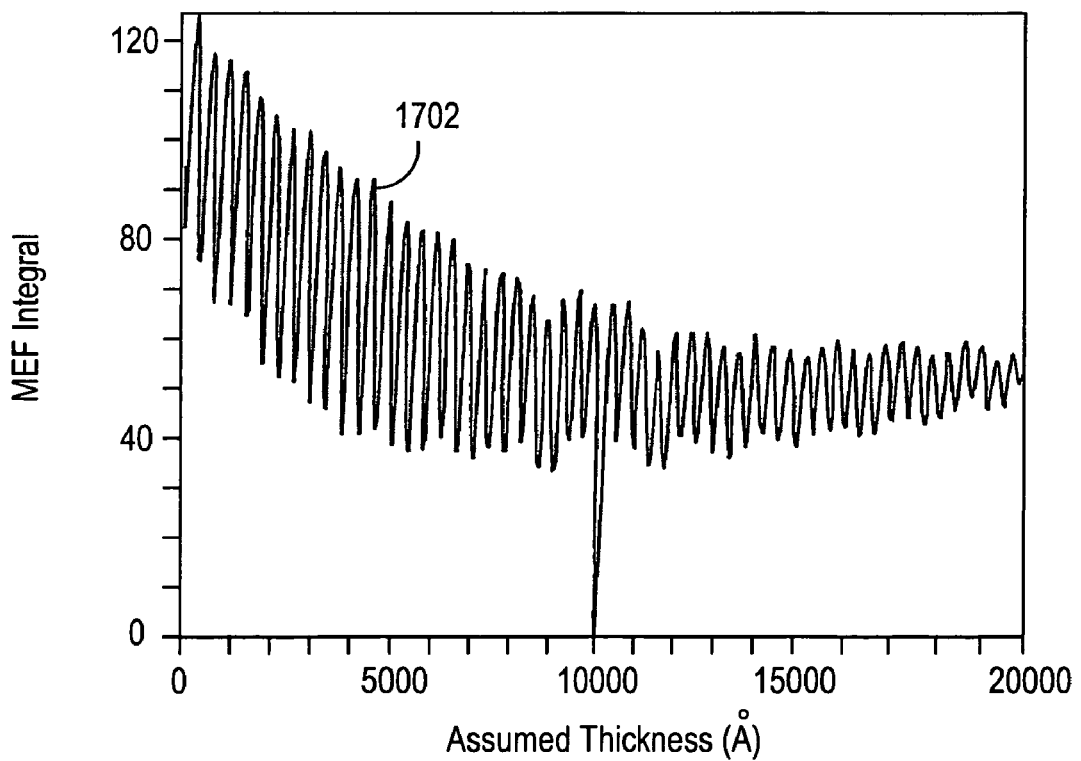
FIG. 17 illustrates a sensitivity plot calculated using an MEF integral for a 10000 Å SiO2/Si sample.

Exploration of a larger parameter space demonstrates why, in some situations, the current invention is best utilized in conjunction with prior art methods. The reasons for this become evident upon examination of FIG. 17 which presents a sensitivity plot 1702 calculated using the current invention for the 10000 Å SiO$_2$/Si sample graphed over a wider range of "assumed" thickness values. While the value of the MEF integral at the "actual" thickness is clearly distinguishable from its value at all other "assumed" thicknesses, the sharp features in the line shape of the MEF integral render it computationally arduous to fit. Hence, it would more efficient to begin searching for the minimum using a Chi-square based merit function and then once apparent convergence had been achieved, switch over and continue searching for the "actual" minimum using the current invention. In this sense the use of the current invention represents a high resolution mode of reflectometer operation.

Figure 18:
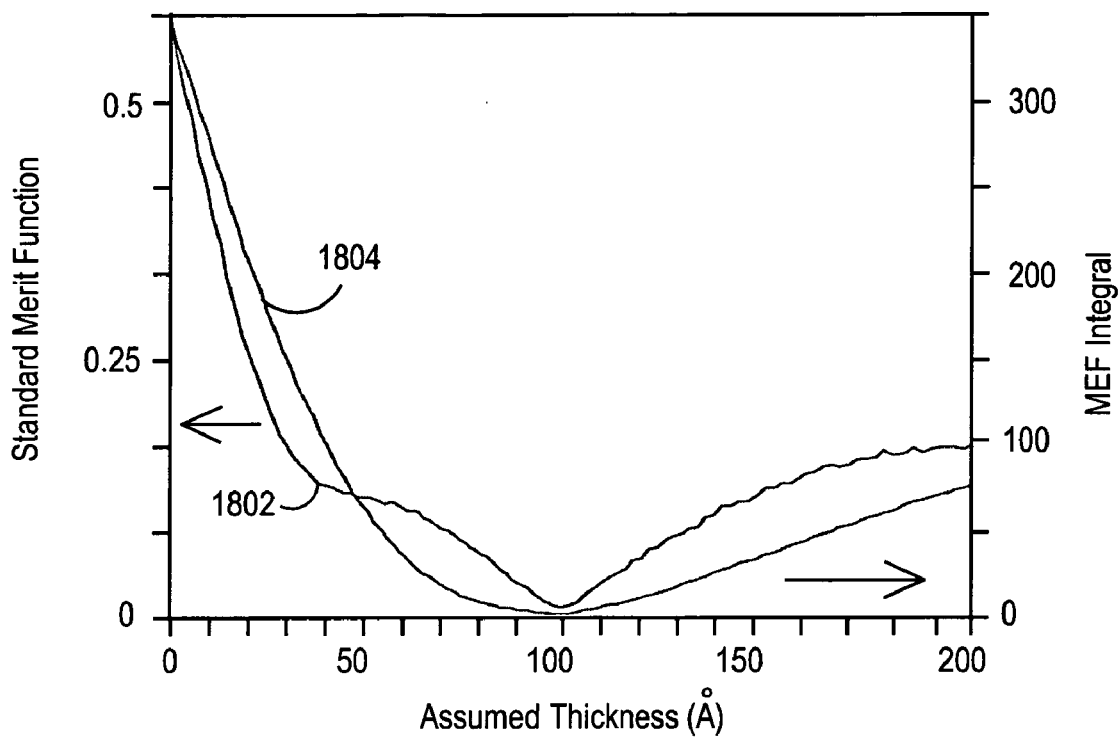
FIG. 18 illustrates a comparison of sensitivity plots calculated using an MEF integral and a standard prior art merit function for a 100 Å SiO2/Si sample.

In other situations, it may be possible to recognize the benefits afforded by the current invention without also employing the use of conventional Chi-square methods. An example of one such situation is the measurement of a 100 Å SiO$_2$/Si sample in the presence of 1% noise in the measured reflectance data. In this circumstance the global search performance of the present invention is comparable to that of the standard Chi-square method. Evidence of this is provided by the sensitivity plot comparison presented in FIG. 18. As shown in FIG. 18, a sensitivity plot 1802 of the standard Chi-square method is compared to a sensitivity plot 1804 utilizing the MEF techniques according to the present invention. While both functions exhibit relatively smooth line shapes it is noted that the influence of the 1% noise in the reflectance data is already evident in the Chi-square results.

Figure 19:
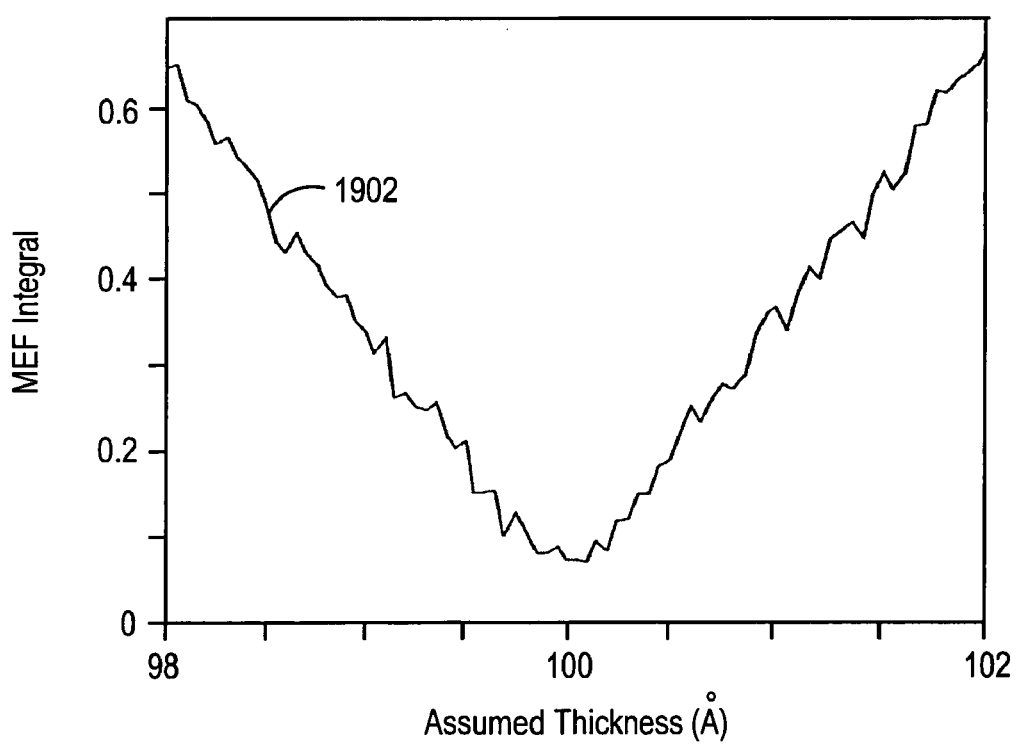
FIG. 19 illustrates an expanded sensitivity plot calculated using an MEF integral for a 100 Å SiO2/Si sample in the presence of 1% noise on the measured reflectance data.
Figure 20:
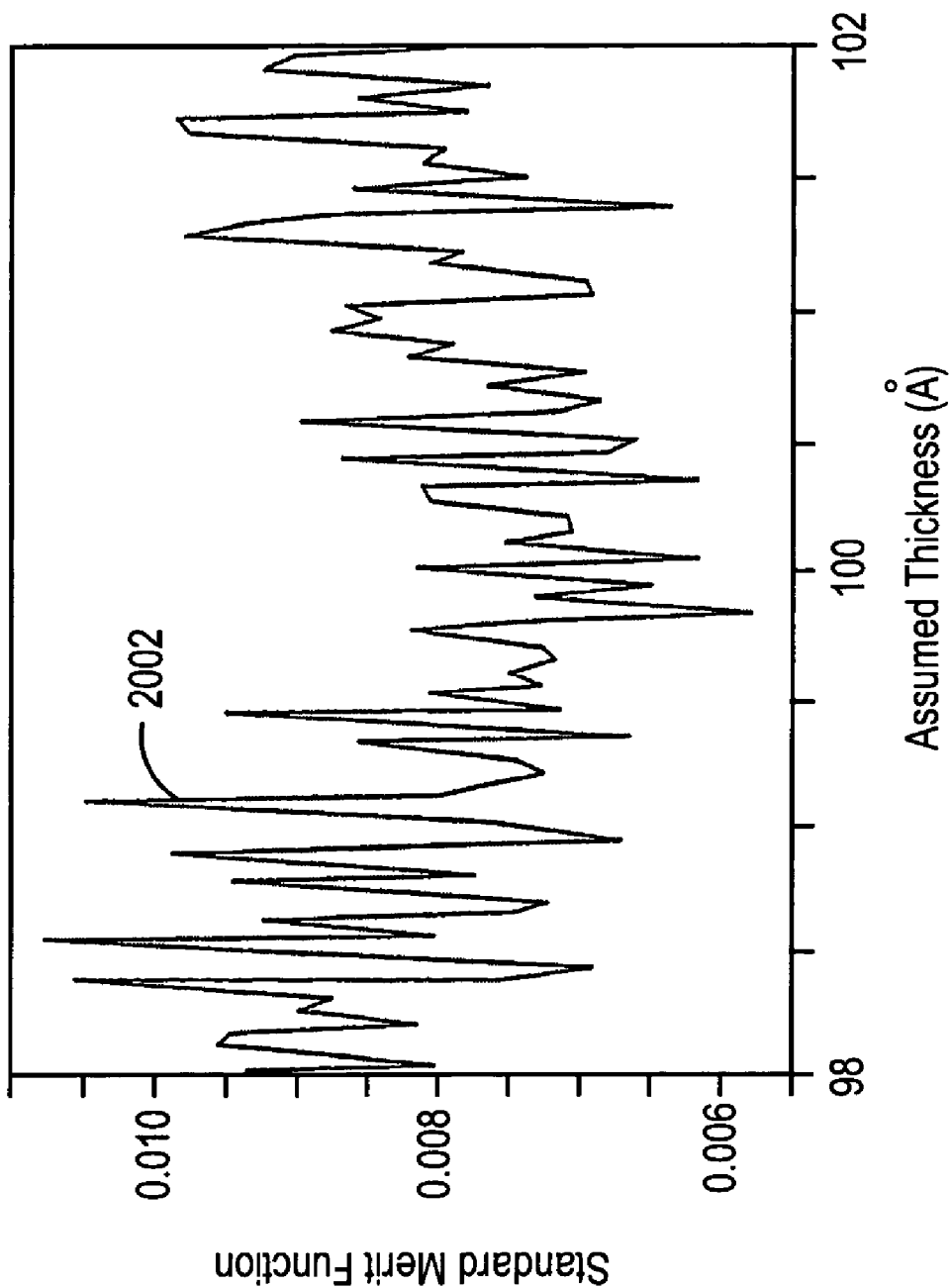
FIG. 20 illustrates an expanded sensitivity plot calculated using standard prior art merit function for a 100 Å SiO2/Si sample in the presence of 1% noise on the measured reflectance data.

FIGS. 19 and 20 present expanded sensitivity plots covering a 4 Å region in the vicinity of the "actual" thickness of the 100 Å SiO$_2$/Si sample calculated using the MEF technique of the present invention (sensitivity plot 1902 of FIG. 19) and the Chi-square method (sensitivity plot 2002 of FIG. 20) respectively. Comparisons of these two figures demonstrate the advantageous performance of the present invention in this situation.

Thus, data measurements may be obtained by utilizing a fitting routine that includes at least a portion of the routine that is a spectrally driven fitting routine rather than relying solely on an amplitude driven routine (which typically incorporates difference calculations). More particularly, measurements may be obtained by utilizing the presence of sharp, narrow spectral features. In one embodiment utilizing a spectral driven routine, a ratio of an expected reflectance spectrum of the sample being measured to the actual reflectance spectrum of the sample being measured. Rather than being based upon a difference between the expected and actual values, the techniques provided herein utilize a ratio of the values. The derivative of this ratio may be utilized to accentuate sharp spectral features.

These spectrally driven techniques are particularly useful in spectral regions that contain sharp spectral features, for example such as the sharp features that thin films often exhibited in the VUV region. Thus, a data convergent technique is provided that may beneficially utilize an absorption edge effect of the material is disclosed. In this manner sharp spectral features, for example resulting from either interference or absorption effects are advantageously utilized to better determine a data minimum that is indicative of an actual measurement value. The merit function presented in the present disclosure may therefore be driven by the absorption properties of the material being measured with an emphasis on regions that encompass large changes in absorption (the absorption edges) for small changes in sample properties.

The data reduction techniques may utilize a two step approach. In such an embodiment a low resolution step such as an amplitude driven fitting routine may be used to first provide a "coarse" measurement. Then a high resolution step such as a spectrally-driven fitting routine that advantageously utilizes the presence of sharp spectral features may be used to then provide a "fine" measurement. In one approach for such a technique, a low resolution approach may be utilized to obtain a rough measurement value by using a difference based technique such as in a "Chi-square" merit function and then a more accurate determination of the actual measurement value may be obtained by utilizing the spectrally driven ratio based technique in the region of interest initially identified by the low resolution technique.

The techniques provided herein may be construed as dynamically weighting the results for regions in which the sharp spectral features are present. For example with regard to sharp spectral edges present in the VUV range, these techniques may be construed as applying a weighting function which strongly emphasizes the VUV and strongly de-emphasizes the DUV and longer wavelength data where sharp spectral features may not be expected for a given sample. Further, the process may be weighted such that only measured data that could reasonably be expected to contain useful information may be included. This weighting method may be dynamic since the decision making process (which measured data should be considered) could be repeated after each iteration.

While the examples presented herein have addressed utilization of the technique to facilitate accurate measurements of film thickness, it will be apparent to those skilled in the art that other preferred embodiments of the invention can be employed equally well in the measurement of other material properties including, but not limited to complex refractive index, composition, porosity, surface or interface roughness, etc. Additionally, while the examples presented herein have dealt specifically with the measurement of SiO$_2$/Si samples, it will be clear that many other types of samples may be measured equally well using the described methods. For example, the techniques provided herein may be utilized when analyzing more complex stacks of thin films. Examples of such stacks include thin film SiO$_2$/SiN stacks on a substrate or thin film SiN/SiO$_2$/SiN stacks on a substrate.

As discussed earlier, the heightened levels of sensitivity afforded by the current invention results largely from the fact that it exploits the substantial changes in reflectance signal that accompany small changes in the properties of samples when in the vicinity of the optical absorption edge of one or more of the materials comprising such samples. While such features commonly lie in the VUV spectral region, the technique can also be generally applied at longer wavelengths in situations where substantially sharp features are expected in the MEF as a result of subtle changes in the physical properties of the samples under study.

It will be recognized by those skilled in the art that many other methods for quantifying the MEF signal in such a manner as to render it useful for feedback to an iterative routine designed to minimize its value through adjustments in the "assumed" properties of the measured sample exist. Furthermore, it will also be readily apparent that in some circumstances additional mathematical steps may be performed to enhance the performance of the measurement routine.

It will be recognized that as described above a calibration technique is provided that may include the use of two calibration samples in the calibration process. Further, the technique allows for calibration even in the presence of variations between the actual and assumed properties of at least one of the calibration samples. In addition, the technique described above includes a calibration technique in which a ratio of the reflected intensity measurements from the first and second calibration samples (for example Iref/Ical as shown in FIG. 12) is utilized.

The use of multiple calibration samples and the ratio of the intensity reflected from the samples may be utilized in a variety of manners to achieve a calibration even under conditions in which changes in the calibration sample and system variations and drift may exist. For example as described above the use of two calibration samples in which a first calibration sample has sharp spectral features in the wavelength region of interest and the second sample is relatively featureless in the wavelength region of interest as compared to the first sample. In another example of the use of two calibration samples, a ratio of the intensity reflected from the first and second calibration samples may be utilized wherein neither of the two calibration samples need to be relatively featureless. In such an embodiment it is merely desirable that the samples be relatively different in their reflective properties at the desired wavelengths as described below in more detail. In such a technique the reflectance data of each sample may then be considered relatively decoupled from the other. The techniques described above with reference to a first sample and a second sample that is relatively featureless are one example of the use of two calibration samples that are relatively different in their reflective properties, however, as described below techniques may be utilized in which neither calibration sample needs to be spectrally featureless.

More particularly, even without an absolute reflectance calibration, the ratio of reflectances from two samples can be measured via the measured intensities, since $$\frac{I_2}{I_1} = \frac{R_2}{R_1} \qquad \text{eq. 3}$$

Environmental or instrument drift will not play a significant role if the intensities are measured from each sample within a short time of one another, so equation 3 arises from the fact that the incident intensity $I_0$ does not change during the two measurements. This ratio can be analyzed using standard thin film regression analysis to extract the same film parameters (n, k, thickness, interface roughness, etc.) that are determined from an absolute reflectance of a single sample. However, unlike in the case of a single intensity, changes in the measured ratio from one measurement to the next are due to changes in the samples themselves, and not to environmental or lamp drift. Thus, the ratio of eq. 3 may be measured at different time intervals to determine changes in the samples independently of changes in $I_0$. This data may then be utilized to calibrate the reflectometer and determine $I_0$.

To gain a better understanding of these techniques an example may be shown with respect to the assumption that the calibration sample changes are due to a changing oxide thickness, or are due to contamination layers that are well described by assuming $SiO_2$ optical properties. It will be recognized that the example calibration samples described herein are merely provided to aid in the understanding of the techniques disclosed and that other calibration samples and thicknesses may be utilized.

Thus, to provide an exemplary description of the calibration techniques, a modified calibration procedure could be constructed using a bare-Si calibration sample in conjunction with a 1000 Å $SiO_2$/Si calibration sample. By measuring the intensities of the two samples, the ratio of the intensities can be analyzed to extract the oxide thicknesses of both samples. The thickness determined for the bare Si calibration sample can be fed back into the calibration procedure of eq. 2 to get a more accurate absolute reflectance.

Figure 21A:
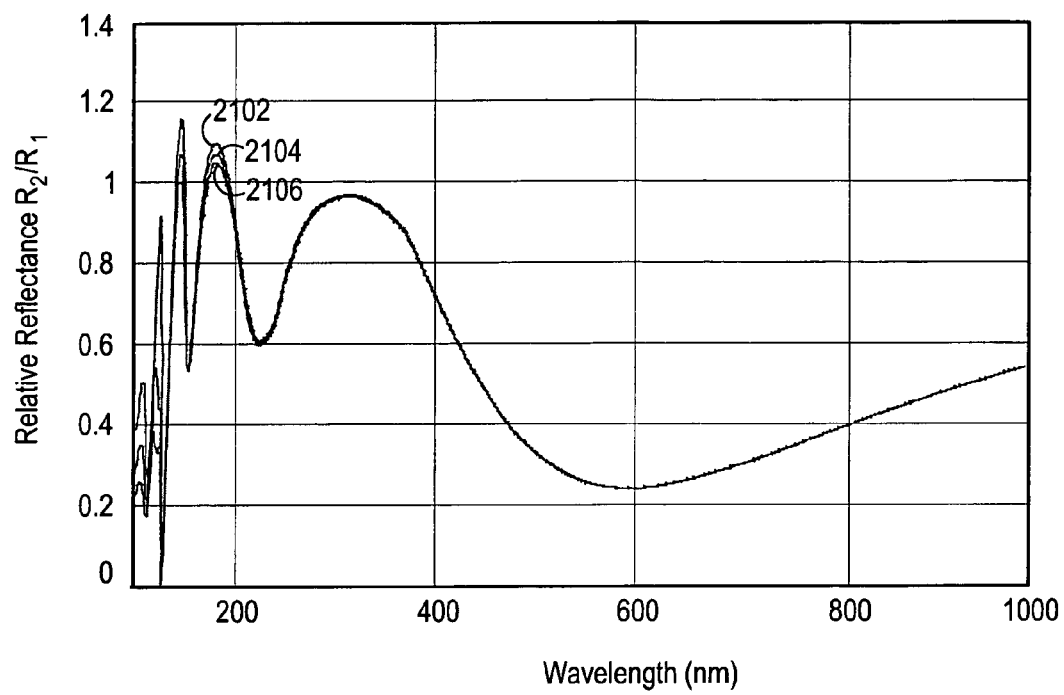
FIGS. 21A and 21B illustrate plots of a relative reflectance ratio of two calibration samples in which a thinner oxide varies on one of the samples.
Figure 21B:
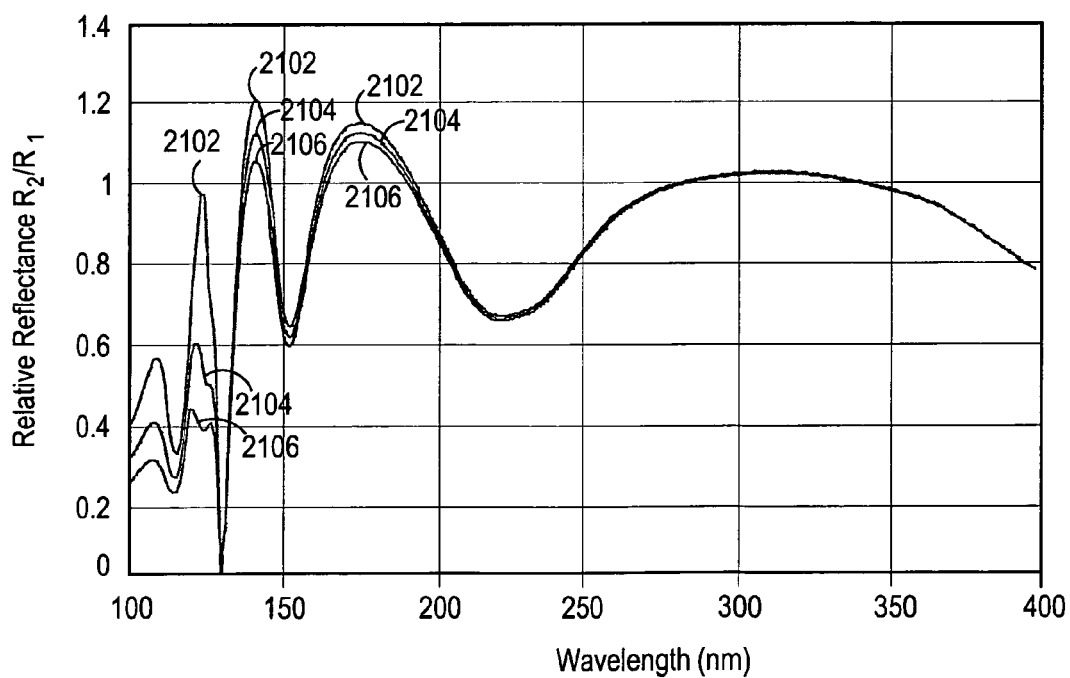

FIGS. 21A, 21B, 22A, and 22B show comparisons of simulated reflectance ratios between a native $SiO_2$/Si calibration sample (Sample 1, corresponding to $R_1$) and a nominally 1000 Å $SiO_2$/Si calibration sample (Sample 2, corresponding to $R_2$). FIGS. 21A and 21B shows the effects of increasing native $SiO_2$ thickness on the ratio $R_2/R_1$. As shown in FIG. 21A, the reflectance ratio $R_2/R_1$ is provided for wavelengths up to 1000 nm while FIG. 21B is an expanded view of the same ratio for wavelengths between 100 nm and 400 nm. In FIGS. 21A and 21B, plots of the impact of a variation in the native oxide on Sample 1 ($R_1$) are shown for 10, 20, and 30 Å of $SiO_2$ in plots 2106, 2104, and 2102 respectively. The main effect of increasing native $SiO_2$ thickness is to increase the ratio in the VUV, since the reflectance $R_2$ is decreased.

Figure 22A:
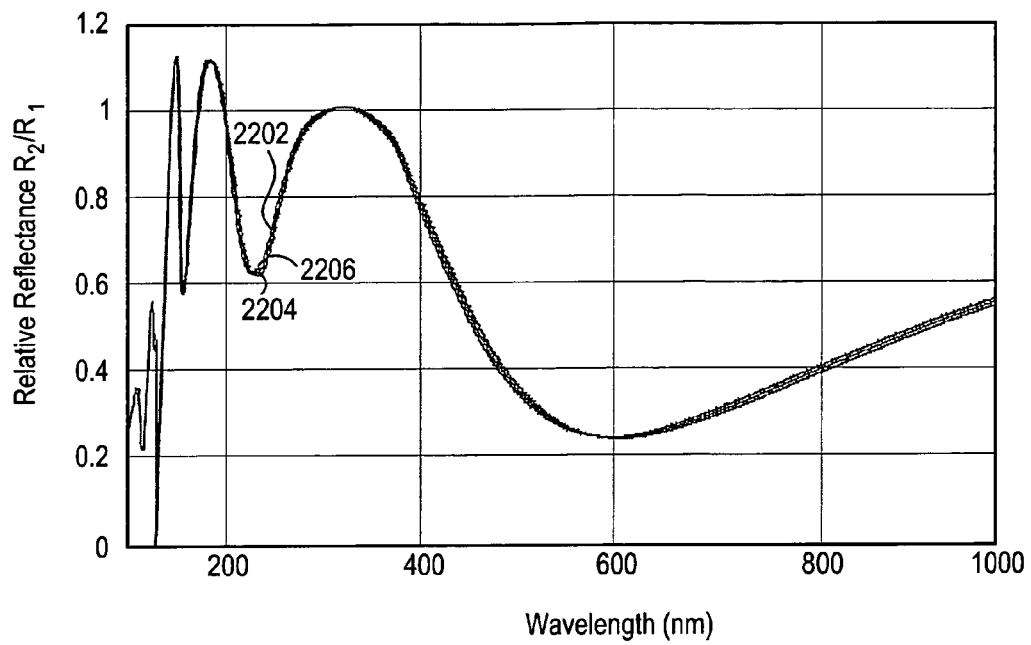
FIGS. 22A and 22B illustrate plots of a relative reflectance of two calibration samples in which a thicker oxide varies on one of the samples.
Figure 22B:
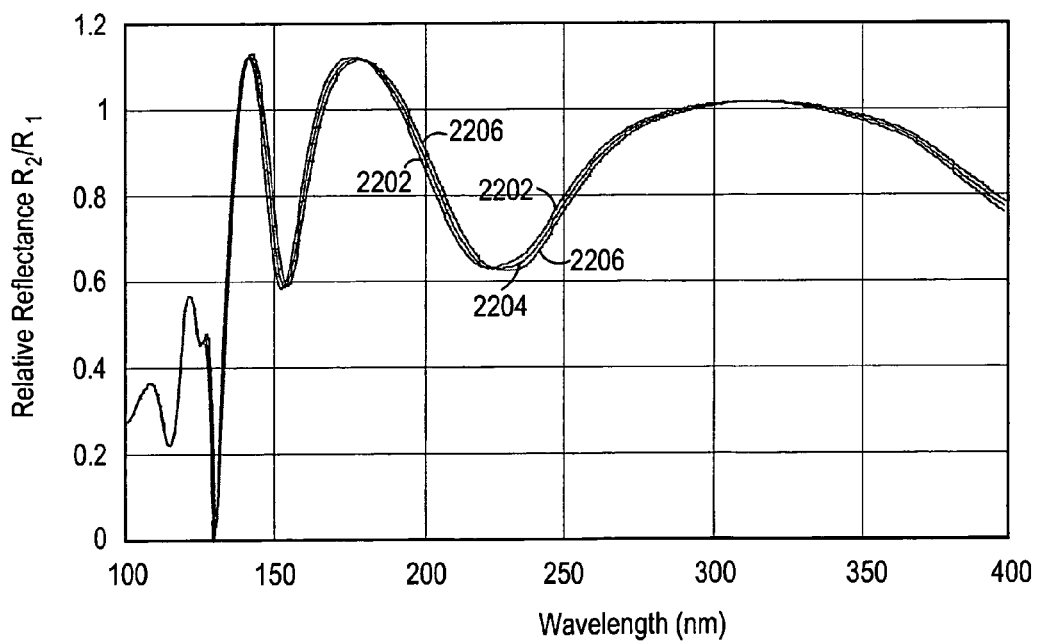

In contrast, the effect of increasing the 1000 Å $SiO_2$ thickness is to shift the interference maxima and minima to longer wavelengths. More particularly, FIGS. 22A and 22B illustrate the effect of variations of Sample 2 of 1000 Å $SiO_2$/Si, 1010 Å $SiO_2$/Si, and 1020 Å $SiO_2$/Si for a constant Sample 1 native oxide of 20 Å. More particularly, plots 2202, 2204 and 2206 show the impact of variations of Sample 2 of 1000 Å $SiO_2$/Si, 1010 Å $SiO_2$/Si, and 1020 Å $SiO_2$/Si respectively (FIG. 22A showing an expanded view of the wavelengths from 100-400 nm). Thus, the thicknesses of the two samples (one thick and one thin) may be considered decoupled, and the thickness of each can be extracted from a standard analysis of the ratio measurement. Moreover, these thicknesses may be extracted from the ratio data without making use of an absolute reflectance standard. Since this ratio is the same regardless of system or lamp drift (assuming the intensities or Sample 1 and Sample 2 are measured in fairly quick succession), differences observed in the ratio over time will correspond to changes in the actual samples. FIGS. 21 and 22 illustrate that if the sample property in question is the $SiO_2$ thickness, the amount of thickness change on each sample can be determined. The thickness of the native oxide layer detected on Sample 2 in this way can then be used to improve the quality of an absolute calibration using that sample.

It is noted that if one of the calibration samples really does stay constant, changes in the reflectance of the other sample can be inferred directly from changes in the ratio. However, in practice the mechanism for the calibration sample drift is a typically a buildup of contamination layer on both samples, so this will usually not be the case.

The technique described herein provides a calibration technique that may be utilized even if the contaminant layer is not merely a growing oxide layer (including for example organic or silicon based contaminants). For the Si calibration samples described above, it may be sufficient to account for the fact that the absolute reflectance is reduced by growing contaminant so that a precise description of the contaminant is not strictly necessary. However, the most accurate calibration models may include distinct contaminant layers on both samples.

Relative reflectance measurements can be used to determine a better optical description of the contaminant layer buildup on calibration samples, and incorporate that information into the calibration procedure. The film structures in the example above may be the contaminant layer/native $SiO_2$/Si of Sample 1 and contaminant layer/1000 Å $SiO_2$/Si of Sample 2, with the contaminant layer thickness determined during the relative reflectance measurement. This will yield not only more stable absolute reflectance calibration, but a more accurate absolute reflectance in the first place.

Figure 23A:
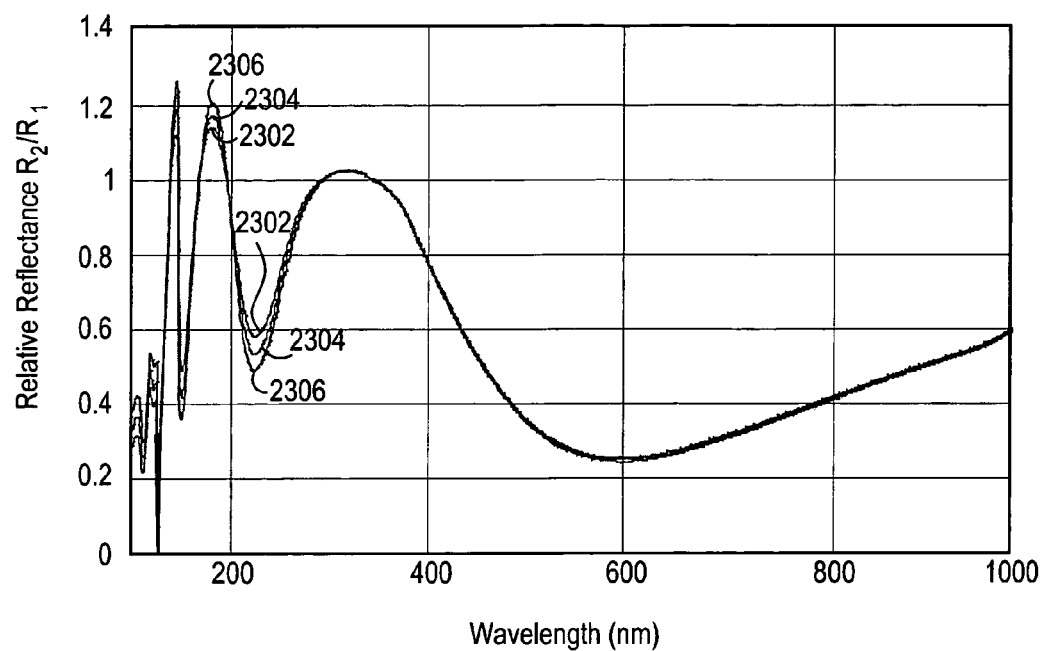
FIGS. 23A and 23B illustrate plots of relative reflectance of two calibration samples with varying thicknesses of a contamination layer.
Figure 23B:
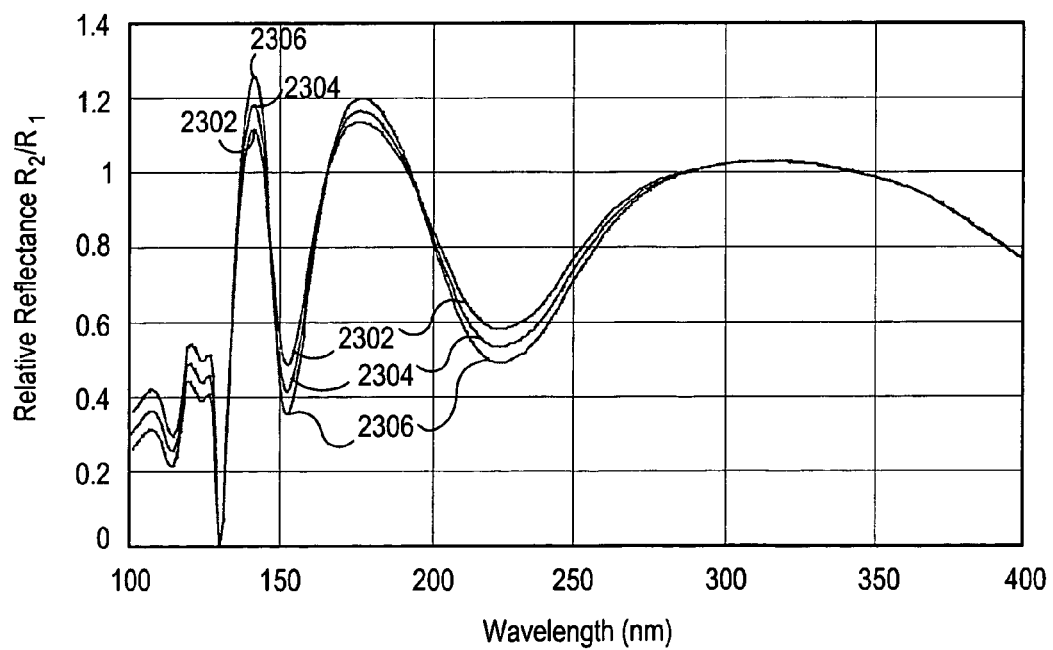

An illustration is provided in FIGS. 23A and 23B of how an contaminant layer buildup might affect the reflectance ratio for different amounts of contaminant. The film structures are contaminant layer/10 Å $SiO_2$/Si for Sample 1 and contaminant layer/1000 Å $SiO_2$/Si for Sample 2. FIG. 23A shows a comparison of $R_2/R_1$ for three different contaminant layer thicknesses of 10 Å, 20 Å, and 30 Å in plots 2302, 2304 and 2306 respectively. One might note that since the contaminant layer optical properties are actually different from those of $SiO_2$, the behavior is decoupled from that shown in FIGS. 21 and 22. In other words, all three parameters—native oxide thickness, thick oxide thickness, and contaminant layer thickness—can be determined simultaneously from a single ratio measurement. The determined thicknesses can be fed back into the calibration procedure of Eq. 2, as before. Obviously, in this case, either or both oxide thicknesses could be fixed to some previously determined value if it is only the contamination layer that is expected to change. In addition, it might be reasonable to constrain the analysis model by assuming that the same amount of contaminant layer is built up on both samples.

In general, as long as the samples are sufficiently different in their reflective properties (so the ratio is not just 1 for all wavelengths), this type of measurement can be used to analyze samples without the influence of an uncertain calibration standard. For example, a relative reflectance measurement may be used to obtain a modified optical description of $SiO_2$ in the VUV region more consistent with the observed ratio.

In the example described above, both samples are formed of the same material (native $SiO_2$ on silicon and thick $SiO_2$ on silicon). An advantage to using the same material for both samples may be that the same contaminant could develop on the surface of both samples. Using samples with different surfaces might cause differences in the contaminant film that develops, making the contaminant layer harder to characterize. However, it will be recognized that the techniques described herein may be utilized with samples having different materials.

Further, it is noted that the example described above provided a technique in which characteristics of Sample 1 (native oxide sample) were determined and then that data used as a calibration standard. However, alternatively characteristics of Sample 2 may be have been determined and that data used as a calibration standard. In one embodiment, it may be more advantageous to use the thicker $SiO_2$ sample for the calibration sample, since any remaining errors are more likely to reveal themselves in the form of artifacts in the vicinity of the $SiO_2$ interference extrema. In general, the film structures could be any structures for which enough information is known to construct a model ratio and either of the samples may be used for the further calibrations.

Figure 24:
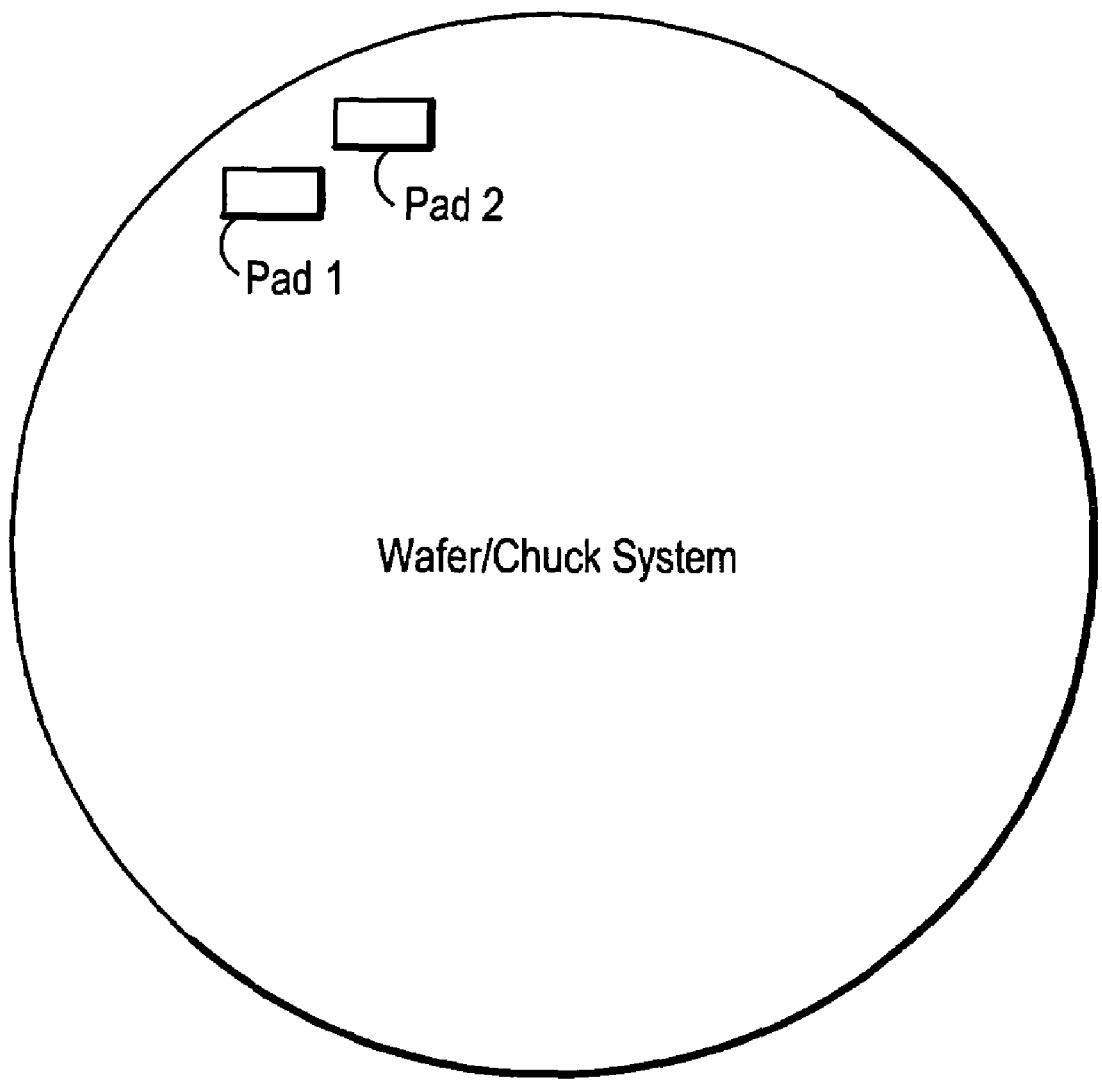
FIG. 24 illustrates an exemplary mechanical implementation of two calibration samples.

The calibration samples, Sample 1 and Sample 2, may be constructed in any number of a wide variety of manners as is known in the art. In one embodiment, the two samples may each be formed on the same substrate. For example, FIG. 24 illustrates a possible mechanical implementation of the calibration procedure in a reflectometer system, with two oxide pads of different thicknesses (such as Sample 1 and Sample 2 in the example above) formed on a semiconductor wafer or mounted on a semiconductor wafer chuck as pad 1 and pad 2. The techniques described herein are not however limited to any particular mechanical implementation of the concepts provided.

The techniques described above thus provides for two calibration samples that are used to provide a relative reflectance ratio $R_2/R_1$ from two samples that have relatively different reflective properties. Utilizing such a technique, changes in the calibration standard over time may occur while still providing an accurate calibration. These techniques may be implemented in a wide variety of manners. Exemplary calibration process flows are described with reference to FIGS. 25 and 26, however, it will be recognized that other steps and flows may be utilized while still taking advantage of the techniques described herein.

Figure 25:
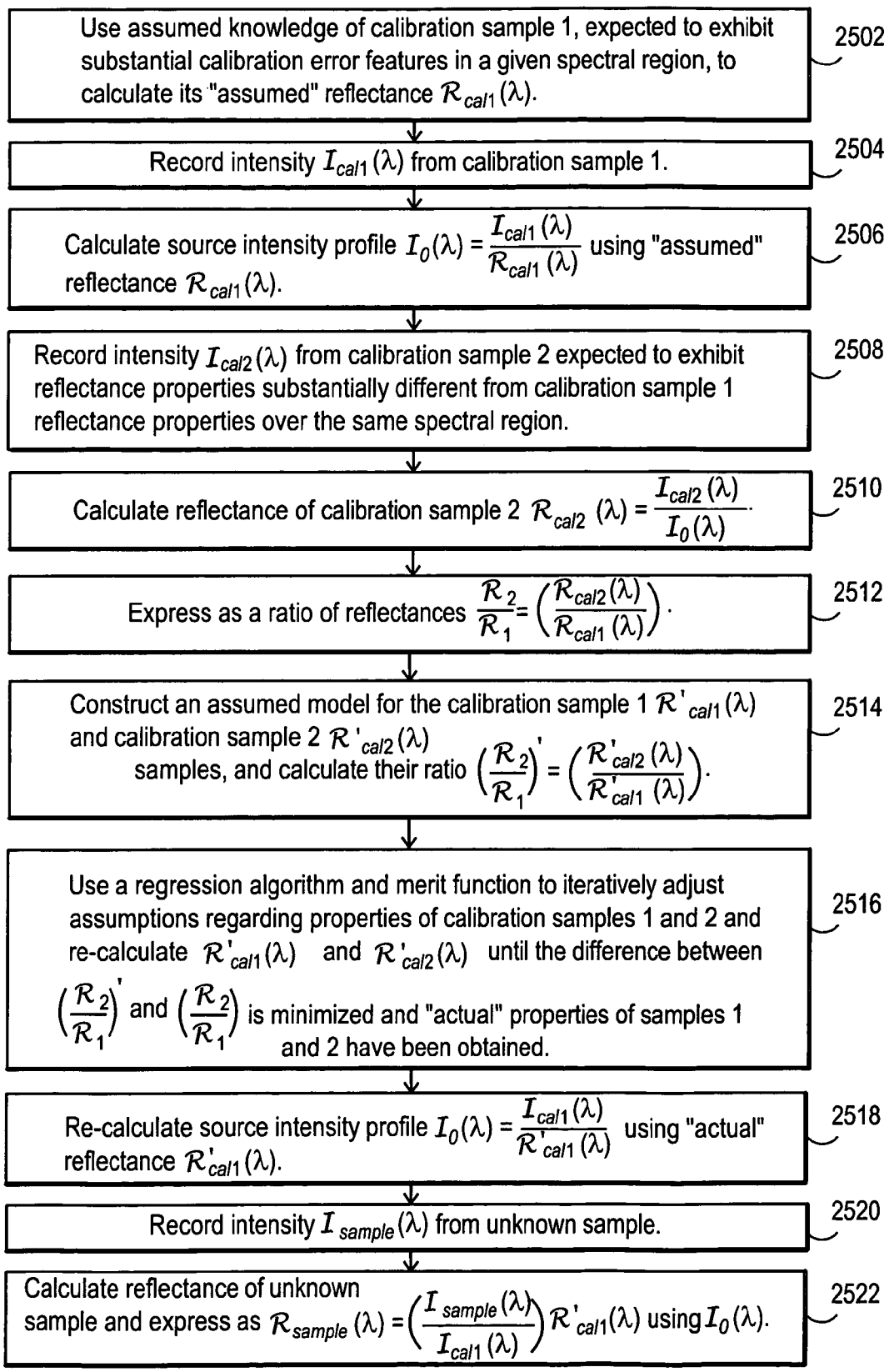
FIG. 25 illustrates a flow chart of an exemplary technique to utilize the reflectance ratio of two calibration samples to calibrate a reflectometer measurement.

As shown in FIG. 25 an exemplary technique in which a reflectometer is calibrated assuming the original reflectance of a first calibration sample is correct and then forming the ratio between the reflectance of the first calibration sample and a second calibration sample. More particularly, in step 2502 an assumed knowledge of calibration sample 1 (expected to exhibit substantial calibration error features in a given spectral region) is used to calculate an assumed reflectance of sample 1. Then in step 2504, the intensity is recorded from calibration sample 1. Next in step 2506 the source intensity profile is calculated using the assumed reflectance of calibration sample 1. In step 2508 the intensity of calibration sample 2 (a sample expected to exhibit reflectance properties substantially different from calibration sample 1 over the same spectral region) is recorded. A reflectance of calibration sample 2 is then calculated at step 2510. A ratio of the reflectances of calibration samples 1 and 2 are then expressed as a ratio in step 2512. An assumed model for the calibration samples 1 and 2 may then be constructed as expressed as a reflectance ratio as shown in step 2514. In step 2516, a regression algorithm and merit function may be used to iteratively adjust assumptions regarding properties of calibration samples 1 and 2 and to recalculate the assumed model reflectances until the difference between the reflectance of the calculated reflectance ratio and the model ratio is minimized and thus the "actual" properties of samples 1 and 2 have been obtained. Then, in step 2518 the source intensity profile may be recalculated using the "actual" reflectance of calibration sample 1. In step 2520, the intensity from an unknown sample may then be recorded and in step 2522 the calculated reflectance of the unknown sample may be expressed as shown.

Figure 26:
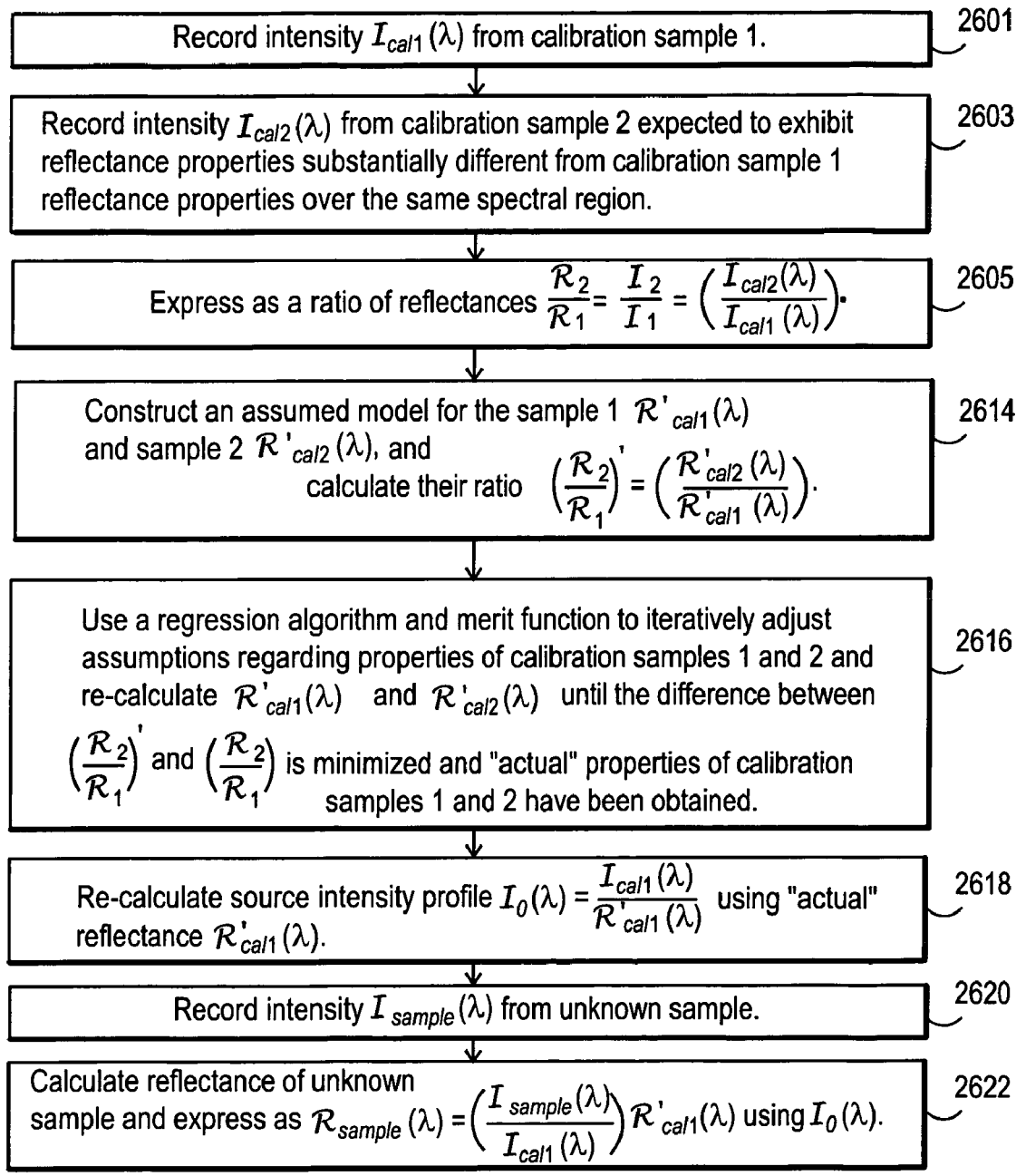
FIG. 26 illustrates another flow chart of an exemplary technique to utilize the reflectance ratio of two calibration samples to calibrate a reflectometer measurement.

Another exemplary calibration flowchart is shown in FIG. 26. As shown in FIG. 26, a simplified process may be utilized wherein the intensities from the two samples are used to directly form the reflectance ratio (in contrast to the technique of FIG. 25 in which an assumed reflectance for one of the samples was calculated from an assumed knowledge of the same sample). As shown in FIG. 26, the intensity is recorded from calibration sample 1 at step 2601. In step 2603 the intensity of calibration sample 2 is recorded (a sample expected to exhibit reflectance properties substantially different from calibration sample 1 over the same spectral region). A ratio of the reflectances of calibration samples 1 and 2 are then expressed as shown in step 2605 based upon the intensities recorded from samples 1 and 2. An assumed model for the calibration samples 1and 2 may then be constructed as expressed as a reflectance ratio as shown in step 2614. In step 2616, a regression algorithm and merit function may be used to iteratively adjust assumptions regarding properties of calibration samples 1 and 2 and to recalculate the assumed model reflectances until the difference between the reflectance of the calculated reflectance ratio and the model ratio is minimized and thus the "actual" properties of samples 1 and 2 have been obtained. Then, in step 2618 the source intensity profile may be recalculated using the "actual" reflectance of calibration sample 1. In step 2620, the intensity from an unknown sample may then be recorded and in step 2622 the calculated reflectance of the unknown sample may be expressed as shown.

It should be pointed out that in analyzing or otherwise discussing the ratio in equation 3, it is convenient to calculate the ratio by first calculating $R_1$ and $R_2$ of the individual samples from standard thin film models. However, it should be obvious that the thin film models could be easily reformulated to apply directly to the ratio $I_1/I_2$, which is mathematically and conceptually equivalent.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as presently preferred embodiments. Equivalent elements may be substituted for those illustrated and described herein and certain features of the invention may be utilized independently of the use of other features, all as would be apparent to one skilled in the art after having the benefit of this description of the invention.

What is claimed is:

1. A method of calibrating a reflectometer, comprising:
providing a first calibration sample and a second calibration sample, wherein the reflectance properties of the first calibration sample and the second calibration sample are different;
collecting a first set of data from the first calibration sample;
collecting a second set of data from the second calibration sample; and
utilizing a ratio of at least a portion of the first set of data and at least a portion of the second set of data to determine a property of at least one of the first and second calibration samples so that reflectance data from an unknown sample may be calibrated.

2. The method of claim 1, wherein the first set of data obtained from the first calibration sample includes intensity data and the second set of data obtained from the second calibration sample includes intensity data.

3. The method of claim 2, wherein a reflectance ratio is obtained from the intensity data of the first and second calibration samples.

4. The method of claim 3, wherein at least one of the first and second calibration samples is expected to exhibit variations from its assumed physical properties.

5. The method of claim 4, wherein an actual reflectance is obtained for at least the one of the first and second calibration samples that is expected to exhibit variations from its assumed physical properties.

6. The method of claim 5, wherein a source intensity profile is obtained through use of the actual reflectance and wherein the reflectance of an unknown sample is calibrated by use of the source intensity profile.

7. The method of claim 3, wherein a source intensity profile is obtained through use of the reflectance ratio and wherein a reflectance of the unknown sample is calibrated by use of the source intensity profile.

8. The method of claim 7, wherein the source intensity profile is obtained by first analyzing the reflectance ratio using thin film models and a regression analysis to adjust one or more properties of one or both of the first and second calibration samples and wherein a result of the analysis is used to derive an absolute reflectance of one or both of the first and second calibration samples, wherein the absolute reflectance is used to obtain the source intensity profile via $I_0=I_{cal}/R_{cal}$, wherein a reflectance of an unknown sample is calibrated by use of the determined source intensity profile via $R=I_r/I_0$.

9. The method of claim 3, wherein one or both of the first calibration sample and the second calibration sample have one or more contaminant layers, wherein one or more properties of the contaminant layers are determined through analysis of the reflectance ratio.

10. The method of claim 1, wherein at least one of the first and second calibration samples is expected to exhibit variations from its assumed physical properties.

11. The method of claim 10, wherein an initial source intensity profile is calculated utilizing an assumed reflectance of the at least one of the first and second calibration samples that are expected to exhibit variations from its assumed physical properties.

12. The method of claim 11, wherein a recalculated source intensity profile is calculated utilizing a calculated actual reflectance of the at least one of the first and second calibration samples that are expected to exhibit variations from its assumed physical properties.

13. The method of claim 10, wherein variations are expected in the assumed physical properties of both the first and second calibration samples.

14. The method of claim 1, wherein the first calibration sample has a thicker oxide as compared to a thinner oxide on the second calibration sample.

15. The method of claim 14, wherein the first calibration sample comprises an SiO2/Si structure and the second calibration sample comprises an SiO2/Si structure.

16. The method of claim 15, wherein the thinner oxide on the second calibration sample is a native oxide.

17. The method of claim 1, wherein the first set of data from the first calibration sample is decoupled from the second set of data from the second calibration sample.

18. The method of claim 1, wherein one or both of the first calibration sample and the second calibration sample have one or more contaminant layers, wherein one or more properties of the contaminant layers are determined through analysis of the ratio.

19. A method of calibrating a reflectometer which operates at wavelengths that include at least some wavelengths below deep ultra-violet (DUV) wavelengths, comprising:
providing a first calibration sample and a second calibration sample, wherein the reflectance properties of the first calibration sample and the second calibration sample are different;

collecting a first set of data from a first calibration sample, the first set of data including at least some intensity data collected for wavelengths below DUV wavelengths;

collecting a second set of data from the second calibration sample, the second set of data including at least some intensity data collected for wavelengths below DUV wavelengths; and utilizing a ratio based on the first set of data and the second set of data to determine a reflectance of at least one of the first calibration sample and the second calibration sample to assist in calibrating the reflectometer at wavelengths that include at least some wavelengths below DUV wavelengths.

20. The method of claim 19, wherein a reflectance ratio is obtained from the intensity data of the first and second calibration samples.

21. The method of claim 20, wherein at least one of the first and second calibration samples is expected to exhibit variations from its assumed physical properties.

22. The method of claim 21, wherein an actual reflectance is obtained for at least the one of the first and second calibration samples that is expected to exhibit variations from its assumed physical properties.

23. The method of claim 22, wherein a source intensity profile is obtained through use of the actual reflectance and wherein the reflectance of an unknown sample is calibrated by use of the source intensity profile.

24. The method of claim 20, wherein a source intensity profile is obtained through use of the reflectance ratio and wherein the reflectance of an unknown sample is calibrated by use of the source intensity profile.

25. The method of claim 20, wherein one or both of the first calibration sample and the second calibration sample have one or more contaminant layers, wherein one or more properties of the contaminant layers are determined through analysis of the reflectance ratio.

26. The method of claim 19, wherein the first calibration sample has a thicker oxide as compared to a thinner oxide on the second calibration sample.

27. The method of claim 26, wherein the first calibration sample comprises an SiO2/Si structure and the second calibration sample comprises an SiO2/Si structure.

28. The method of claim 27, wherein the thinner oxide on the second calibration sample is a native oxide.

29. The method of claim 19, wherein:
an assumed reflectance of the first calibration sample and the first set of data are utilized to calculate an initial source intensity profile,
a reflectance of the second calibration sample is obtained utilizing the second set of data and the initial source intensity profile,
a ratio of assumed reflectance of the first calibration sample and the obtained reflectance of the second calibration sample is used to determine an actual property of the first calibration sample, and
a recalculated source intensity profile is obtained utilizing a reflectance of the first calibration sample that is based upon the determined actual property.

30. The method of claim 29 wherein the actual property of the first calibration sample is a material thickness.

31. The method of claim 19, wherein the reflectance properties of the first and second calibration samples are decoupled from each other such that actual physical properties of at least one of the first and second calibration samples may be calculated based upon the obtained intensity data of the first and second calibration samples.

32. The method of claim 19, wherein:
the ratio is based upon a ratio of intensities obtained from the first and second calibration samples,
a source intensity profile is obtained through use of the ratio, and a reflectance of a unknown sample is calibrated by use of the source intensity profile.

33. The method of claim 19, wherein at least one of the first and second calibration samples is expected to exhibit variations from its assumed physical properties.

34. The method of claim 19, wherein one or both of the first calibration sample and the second calibration sample have one or more contaminant layers, wherein one or more properties of the contaminant layers are determined through analysis of the ratio.

35. A method of analyzing reflectometer data, comprising:
providing a first reflectometer sample and at least a second reflectometer sample, wherein the optical response properties of the first reflectometer sample and the second reflectometer sample are different;
collecting a first set of optical response data from the first reflectometer sample;
collecting a second set of optical response data from the second reflectometer sample; and
determining at least one property of at least one of the first and second reflectometer samples by utilizing the first set and second set of optical response data in a manner independent of an incident reflectometer intensity that is utilized when collecting the first and second set of optical response data,
wherein a source intensity profile is obtained through use of a ratio of intensities obtained from the first and second reflectometer samples, and a reflectance of a unknown sample is calibrated by use of the source intensity profile.

36. The method of claim 35, wherein the property is a variation in a physical property of at least one of the first and second reflectometer samples.

37. The method of claim 36, wherein at least one of the first and second reflectometer samples is a calibration sample.

38. The method of claim 37, wherein the first and second reflectometer samples are both calibration samples.

39. The method of claim 35, wherein the determining step further comprises:
utilizing a ratio of at least a portion of the first set of optical response data and at least a portion of the second set of optical response data.

40. The method of claim 39, wherein the ratio is based on the optical intensity measured from the first sample and the second sample.

41. The method of claim 39, wherein utilization of the ratio allows for determination of a change in the at least one property.

* * * * *